United States Patent [19]

Kitamura et al.

[11] Patent Number: 4,743,547

[45] Date of Patent: May 10, 1988

[54] METHOD OF PRODUCING L-PHENYLALANINE

[75] Inventors: Takanori Kitamura; Yoichi Matsumoto; Noriaki Yoshimura, all of Kurashiki, Japan

[73] Assignee: Kuraray Co., Ltd., Kurashiki, Japan

[21] Appl. No.: 849,859

[22] Filed: Apr. 9, 1986

[30] Foreign Application Priority Data

Apr. 9, 1985 [JP] Japan .................................. 60-76126
May 15, 1985 [JP] Japan ................................ 60-104735
Jun. 5, 1985 [JP] Japan ................................ 60-123393
Aug. 30, 1985 [JP] Japan ................................ 60-192441

[51] Int. Cl.$^4$ ........................ C12P 13/22; C07P 41/00
[52] U.S. Cl. ..................................... 435/108; 435/280
[58] Field of Search ................................ 435/280, 108

[56] References Cited

PUBLICATIONS

Kitahara et al.–Chem. Abst. vol. 99 (1983) p. 49767p.
Ermolaev et al.–Chem. Abst. vol. 93 (1980) p. 219,329t.

Primary Examiner—Sam Rosen
Attorney, Agent, or Firm—Oblon, Fisher, Spivak, McClelland & Maier

[57] ABSTRACT

There is provided a method of producing L-phenylalanine in high optical purity which comprises treating an N-acylphenylalanine alkyl ester in L form, in the presence of water, with an enzyme capable of hydrolyzing the N-acylphenylalanine alkyl ester in L form to give L-phenylalanine.

29 Claims, No Drawings

METHOD OF PRODUCING L-PHENYLALANINE

BACKGROUND OF THE INVENTION

1. Field of the Invention

This invention relates to a method of producing L-phenylalanine by treating an N-acylphenylalanine alkyl ester in L form with an enzyme in the presence of water.

2. Description of the Related Art

Various methods are so far known for producing L-phenylalanine by treatment of an L-phenylalanine precursor with an enzyme. For instance, for producing L-phenylalanine by treating an L-phenylalanine precursor with an hydrolyzing enzyme, there are known, among others, a method which comprises treating an N-acyl-DL-phenylalanine with aminoacylase to thereby selectively hydrolyze an N-acyl-L-phenylalanine alone for conversion thereof to L-phenylalanine [cf. U.S. Pat. No. 3,386,888 and Bull. Agr. Chem. Soc. Japan, 21, 300 (1957)], a method which comprises treating a DL-phenylalanine alkyl ester with esterase to selectively hydrolyze an L-phenylalanine alkyl ester alone for conversion to L-phenylalanine [cf. J. Biol. Chem., 203, 755 (1953)], and a method which comprises hydrolyzing 75-benzylhydantoin by treatment with hydantoinase for its conversion to L-phenylalanine (cf. Japanese Patent Publication No. 2274/79). Also known as an alternative is a method which comprises treating an N-acyl-DL-phenylalanine methyl ester with serine proteinase or esterase to thereby selectively hydrolyze an N-acyl-L-phenylalanine methyl ester alone to give the corresponding N-acyl-L-phenylalanine, separating the latter from the unreacted N-acyl-D-phenylalanine methyl ester and hydrolyzing the same with hydrochloric acid for conversion thereof to L-phenylalanine [cf. U.S. Pat. No. 4,262,092 and Synthesis, 1041 (1983)].

Hydrolyzing enzymes, such as aminoacylase and esterase, in many cases exhibit high hydrolyzing activity under nearly neutral conditions. Therefore, for treating acidic or basic L-phenylalanine precursors such as an N-acyl-DL-phenylalanine or a DL-phenylalanine alkyl ester with such hydrolyzing enzymes, it is necessary to adjust the pH of a starting material-containing solution to a value near neutrality in advance by adding a base or an acid to said solution. The reaction mixture obtained by such hydrolysis contains, in addition to L-phenylalanine, which is the desired product, an unreacted N-acyl-D-phenylalanine or an unreacted D-phenylalanine alkyl ester, which occurs as a salt with the above-mentioned base or acid. Generally, L-phenylalanine crystallizes out from such reaction mixture. In that case, also the above salt is ready to crystallize out, so that, for recovering L-phenylalanine in a satisfactorily high purity, a complicated separation process is required. Furthermore, the above-mentioned method of producing L-phenylalanine which starts with an N-acyl-DL-phenylalanine is disadvantageous in that the salt of the N-acyl-DL-phenylalanine with a base tends to inhibit the enzyme activity in the reaction system to thereby cause marked decrease in enzyme activity. In the method of producing L-phenylalanine which uses a DL-phenylalanine alkyl ester as the starting material, the use of a lower alkyl ester of DL-phenylalanine is preferable because of quick formation of L-phenylalanine but disadvantageous in that the lower alkyl ester of DL-phenylalanine is easily converted to DL-phenylalanine by hydrolysis other than the hydrolysis under the action of esterase, so that it is difficult to attain a satisfactory high optical purity of L-phenylalanine using such starting material.

The method of producing L-phenylalanine which comprises treating 5-benzylhydantoin with hydantoinase has drawbacks that the starting material, namely 5-benzylhydantoin, is expensive and that the hydantoinase used is not satisfactorily active.

The method of producing L-phenylalanine which comprises treating an N-acyl-DL-phenylalanine methyl ester with serine proteinase or esterase, separating the resulting N-acyl-L-phenylalanine from the unreacted N-acyl-D-phenylalanine methyl ester and hydrolyzing the former with hydrochloric acid is disadvantageous in that the independent performance of hydrolysis of the ester residue and hydrolysis of the acid amide residue in the N-acylphenylalanine methyl ester makes the process troublesome.

SUMMARY OF THE INVENTION

An object of the invention is to provide a novel method of producing L-phenylalanine. Another object of the invention is to provide a method of producing L-phenylalanine with high purity in an easy and simple manner. A further object of the invention is to provide a commercially advantageous method of producing L-phenylalanine in which a L-phenylalanine precursor readily available on the commercial scale, is used as substrate.

These and other objects are accomplished by providing a method of producing L-phenylalanine which comprises bringing the L form of an N-acylphenylalanine alkyl ester having the general formula

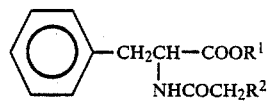 (I)

wherein $R^1$ is a lower alkyl group and $R^2$ is a hydrogen atom, a lower alkyl group or a halogen atom, into contact with an enzyme capable of hydrolyzing said L-form of an N-acylphenylalanine alkyl ester into L-phenylalanine, in the presence of water to thereby cause formation of L-phenylalanine.

DETAILED DESCRIPTION OF THE INVENTION

Referring to the above general formula (I), detailed mention is now made of $R^1$ and $R^2$. $R^1$ is a lower alkyl group. The lower alkyl group is preferably a straight-chain or branched-chain alkyl group containing 1–4 carbon atoms, such as methyl, ethyl, propyl, isopropyl, butyl, isobutyl and or sec-butyl. $R^2$ is a hydrogen atom, a lower alkyl group or a halogen atom. Preferred examples of the lower alkyl group which contain 1–4 carbon atoms and may be straight or branched are methyl, ethyl, propyl, isopropyl and butyl. Chlorine and bromine atoms are preferred examples of said halogen atom. Typical examples of the N-acylphenylalanine alkyl ester of general formula (I) (hereinafter referred to as "APAE") are N-acetylphenylalanine alkyl esters such as N-acetylphenylalanine methyl ester, N-acetylphenylalanine ethyl ester, N-acetylphenylalanine isopropyl ester and N-acetylphenylalanine butyl ester; N-propionylphenylalanine alkyl esters such as N-propionylphenylalanine methyl ester, N-propionylphenylalanine ethyl ester and N-propionylphenylalanine butyl ester; N-butyrylphenylalanine alkyl esters such as N-butyrylphenylalanine methyl ester and N-butyrylphenylalanine ethyl ester; N-valerylphenylalanine alkyl esters such as N-valerylphenylalanine methyl ester; N-hexanoylphenylalanine alkyl esters such as N-hexanoylphenylalanine methyl ester; N-(chloroacetyl)phenylalanine alkyl esters such as N-(chloroacetyl)phenylalanine methyl ester, N-(chloroacetyl)phenylalanine ethyl ester, N-(chloroacetyl)phenylalanine isopropyl ester and N-(chloroacetyl)phenylalanine butyl ester; and N-(bromoacetyl)phenylalanine alkyl esters such as N-(bromoacetyl)phenylalanine methyl ester and N-(bromoacetyl)phenylalanine ethyl ester. These APAE in their L form are used as the starting materials in the L-phenylalanine formation reaction according to the present invention. When those L-form of N-acylphenylalanine alkyl esters in which, in the above general formula (I), $R^1$ is an alkyl group containing 5 or more carbon atoms or $R^2$ is other than a hydrogen atom, a lower alkyl group or a halogen atom are used as starting materials, the rate of enzymatic hydrolysis is unsatisfactorily slow, hence favorable reaction results can hardly be obtained. In carrying out the L-phenylalanine formation reaction in accordance with the invention, the L form of an APAE may be used as the starting material either alone or in the form of a mixture thereof with a D-form of APAE. Convenient is the use of the racemic modification of an APAE which can be readily obtained on a commercial scale by a chemical synthesis, as mentioned later herein.

Any enzyme capable of selectively hydrolyzing the L form of an APAE to give L-phenylalanine can be used as the enzyme for forming L-phenylalanine in accordance with the invention, irrespective of origin, purity, etc. The enzyme may be used in the form of an animal- or plant-derived homogenate, microbial cells, whether disrupted or not, or an extract therefrom. Such enzyme may suitably be selected from among aminoacylase produced by microorganisms such as fungi belonging to the genera Aspergillus, Penicillium, etc., bacteria belonging to the genera Achromobacter, Pseudomonas, Micrococcus, Alcaligenes, etc. and actinomycetes belonging to the genera Streptomyces, etc. and other enzymes. In particular, aminoacylase produced by a fungus belonging to the genus Aspergillus is preferred since it is excellent in hydrolase activity. A fairly large number of enzymes inclusive of the above aminoacylase which are suited for use in the practice of the invention are currently produced on a commercial scale. Examples of such commercially available enzymes are aminoacylase species derived from fungi belonging to the genus Aspergillus [e.g. Acylase "Amano" (Amano Pharmaceutical Co., Ltd.) and Aminoacylase (Tokyo Kasei Kogyo Co., Ltd.)], among others. The L-phenylalanine formation reaction according to the present invention is carried out in a homogeneous reaction system consisting of an aqueous layer alone or in a heterogeneous system consisting of an aqueous layer and an organic layer. The enzyme is used generally in an amount such that its concentration in the aqueous layer amounts to about 0.01–3 percent by weight. The enzyme may be added to the reaction system either as it is or in the immobilized form prepared by immobilizing said enzyme on a carrier by any known immobilization method such as the covalent bond method, crosslinking method or entrapment method. As typical examples of such carrier, there may be mentioned diethylaminoethyl-Sephadex, carrageenan, polyacrylamide, gelatin, fibroin, alginic acid salts, diethylaminoethylcellulose, porous glass, active alumina, hydroxyapatite, ion exchange resins, and light-curable resins based on such a prepolymer as polyethylene glycol diacrylate or polypropylene glycol diacrylate.

The amount of water to be present in the reaction system for the L-phenylalanine formation according to the invention is not critical. Thus, water can be used in an amount such that the APAE concentration does not exceed the saturation concentration, i.e. solubility, or such that it exceeds the saturation concentration. In the latter case, the reaction system occurs as a heterogeneous liquid-solid two-phase system composed of a saturated aqueous APAE solution and that portion of APAE which remains undissolved and this never becomes an obstacle to the performance of the L-phenylalanine formation reaction according to the invention. The saturation concentration of APAE, if this is N-acetylphenylalanine methyl ester, is 1.26 grams per 100 ml of water at 23° C.

In carrying out the L-phenylalanine formation reaction according to the invention, an organic solvent may be present in the reaction system in addition to water. When a water-miscible organic solvent is used as said organic solvent, the solubility of APAE in the water layer can be improved. Therefore, the use of a water-miscible organic solvent makes it possible for an APAE to be dissolved in the enzyme-containing aqueous layer in an increased concentration to thereby cause formation of L-phenylalanine more efficiently. Usable examples of the water-miscible organic solvent are lower alcohols such as methanol, ehtanol and propanol; ketones containing not more than 4 carbon atoms such as acetone and methyl ethyl ketone; cyclic ethers such as tetrahydrofuran and dioxane; and alkylene glycols and monoethers and diethers thereof, such as ethylene glycol, diethylene glycol, ethylene glycol dimethyl ether, diethylene glycol dimethyl ether and triethylene glycol monobutyl ether. When an organic solvent substantially immiscible with water is used in the reaction system, said reaction system becomes a two-layer system consisting of an aqueous layer and an organic layer. In such reaction system, the starting material APAE is distributed predominantly in the organic layer and, therefore, by selecting the organic solvent and the amount thereof adequately, the APAE concentration in the aqueous layer in which an enzyme is present can be maintained constantly at an appropriate level at which the APAE can come into sufficient contact with the enzyme and at the same time can be prevented from inhibiting the enzyme activity. The use of such water-immiscible organic solvent enables not only quick formation of L-phenylalanine but also stable maintenance of the enzyme activity for a prolonged period of time. Examples of such water-immiscible organic solvent are halogenated hydrocarbons such as methylene chloride, carbon tetrachloride, ethylene dichloride and chlorobenzene; nitriles containing not less than 3 carbon atoms, such as benzonitrile and propionitrile; carboxylic acid esters containing not less than 4 carbon atoms, such as ethyl acetate, butyl acetate, methyl propionate and diethyl adipate; ketones containing not less than 5 carbon atoms, such as diethyl ketone, methyl isobutyl ketone, 3-heptanone and acetophenone; ethers containing not less than 5 carbon atoms, such as ethyl propyl ether, anisole, dibutyl ether, phenetole and diphenyl ether; aromatic hydrocarbons containing not less than 6 carbon atoms, such as benzene, toluene and xylene; alcohols containing not less than 6 carbon atoms, such as 1-hexanol and 1-octanol; phosphoric acid triesters containing not less than 8 carbon atoms, such as tributyl phosphate and trioctyl phosphate; and tertiary amines containing not less than 8 carbon atoms in which at least one of the substituents on the nitrogen atom is an aromatic hydrocarbon residue, such as N,N-dimethylaniline and dimethylbenzylamine. Among them, preferred in particular from the rapidity of L-phenylalanine formation viewpoint are carbon tetrachloride, diethyl adipate, methyl isobutyl ketone, 3-heptanone, anisole, phenetole, 1-octanol, tributyl phosphate, trioctyl phosphate, N,N-dimethylaniline and the like. When such water-immiscible organic solvent is used, the volume ratio between the organic layer and the aqueous layer in the reaction system is generally, though not critical, within the range of about 1/10 to about 3/1, preferably within the range of about 1/10 to about 1/1, and is selected within said range depending on the solubility of the starting APAE in the organic solvent employed.

The L-phenylalanine formation reaction according to the present invention is desirably carried out under such pH conditions as to allow the enzyme used to exhibit sufficiently high hydrolase activity. The pH of the aqueous layer in the reaction system is suitably adjusted depending on the kind of enzyme generally within the range of about 4–10, preferably within the range of 5–9, more preferably within the range of 6–8. For adjusting the pH of the aqueous layer, inorganic acids such as hydrochloric acid, sulfuric acid and phosphoric acid; organic acids such as formic acid, acetic acid, propionic acid and benzenesulfonic acid; alkali metal or alkaline earth metal hydroxides or carbonates such as sodium hydroxide, potassium hydroxide, barium hydroxide, sodium carbonate, potassium carbonate and sodium hydrogen carbonate; ammonia; amines such as triethylamine; and buffers such as phosphate buffers, Tris buffers and McIlvaine's buffer may be added unless they adversely affect the enzyme activity. With the progress of the L-phenylalanine formation reaction according to the invention, the carboxylic acid, such as acetic acid, resulting from hydrolysis of the L-form of APAE is accumulated in the reaction system, so that the pH of the aqueous layer in the reaction system tends to decrease. The above-mentioned buffers can inhibit such pH decrease in the aqueous layer during reaction and are thus particularly preferred. It is also preferable to carry out the L-phenylalanine formation reaction at an optimum temperature for the manifestation of enzyme activity. Thus, said reaction is generally carried out within the temperature range of about 20°–60° C., preferably within the range of 25°–40° C. In some instances, addition of a trace amount of a metal ion to the reaction system can increase the enzyme activity. In particular, the presence of the cobalt ion in the reaction system in a concentration within the range of about $10^{-4}$ to $10^{-2}$ mole per liter is preferred.

In the practice of the invention, the L-phenylalanine formation reaction can be conducted batchwise using a stirring, shaking or other mixing means. Said reaction can also be conducted continuously by adding, with the progress of reaction, the starting L-form of APAE, water, the enzyme and so on to the reaction sytem while withdrawing a part or the whole of the reaction mixture containing the product L-phenylalanine from the reaction system. When the reaction system is free of any water-immiscible organic solvent, said reaction can also be performed continuously by passing an aqueous solution containing the L-form of APAE through a column packed with an immobilized enzyme.

L-phenylalanine can be separated easily from the reaction mixture obtained as a result of the L-phenylalanine formation reaction, for example, in the manner of crystallization by taking advantage of the low solubility of L-phenylalanine in water as well as in organic solvents. The unreacted L-form of APAE or a mixture of the same and the D-form can be recovered from the reaction mixture as well. For APAE recovery from the reaction mixture, the high distributability of APAE in the organic layer in a two layer system consisting of water and a water-immiscible organic solvent is utilized. Thus, when the L-phenylalanine formation reaction is conducted in the absence of a water-immiscible organic solvent, the reaction mixture or the distillation residue obtained by removing from said mixture the lower alcohol, which is a by-product of hydrolysis of the L-form of APAE, or the like by distillation, for instance, as necessary is brought into contact with a water-immiscible organic solvent, whereby the APAE can be extracted into the organic layer. When the L-phenylalanine formation reaction is carried out in the presence of a water-immiscible organic solvent, the reaction mixture then obtained already occurs as a heterogeneous system consisting of an APAE-containing organic layer and an L-phenylalanine-and enzyme-containing aqueous layer, so that phase separation can result in easy separation of these. The order of the above-mentioned L-phenylalanine separation from the reaction mixture and APAE separation from said mixture is not critical but either separation procedure may be conducted first. The aqueous layer after separation of L-phenylalanine by crystallization contains the enzyme, which is still active, and a low concentration of L-phenylalanine. It is therefore advantageous to recycle such enzyme-containing aqueous layer for reuse as the reaction medium to the L-phenylalanine formation reaction system. Particularly when the reaction is conducted in the presence of water and a water-immiscible organic solvent, recycling for reuse of the above aqueous layer is preferred from the practical viewpoint since, as mentioned above, the enzyme hardly loses its activity during reaction.

The APAE, on the other hand, is recovered into the organic layer, as mentioned above. Since the L-phenylalanine formation reaction consumes the L-form of APAE, the proportion of the L-form to the D-form in the thus-recovered APAE is lower as compared with that in the APAE used as the starting material. Although the unreacted L-form in the recovered APAE may be recycled for reuse as the starting material to the reaction system, it is advantageous if the proportion of the L-form in said APAE is lower than 50 percent, to subject said APAE to racemization and use the resulting racemic modification as a part of the starting material for the above-mentioned L-phenylalanine formation reaction.

A method found by the present inventors can racemize an optically active APAE in high racemization yield by treatment with a strongly basic amine.

The strongly basic amine to be used in the above-mentioned racemization preferably shows a pH value of not less than 12.0, more preferably a pH value of not less than 12.5, at a temperature of 25° C. in an aqueous solution thereof in a concentration of 0.1 mole per liter. Examples of such strongly basic amine are 1,8- diazabicyclo[5.4.0]undecene-7 (hereinafter referred to as "DBU"; pH value: 12.8), 1,5-diazabicyclo[4.3.0]nonene-5 (hereinafter referred to as "DBN"; pH value: 12.7) and 1,1,3,3-tetramethylguanidine (hereinafter referred to as "TMG"; pH value: 12.7), among which DBU is particularly preferred. The strongly basic amine is used generally in an amount of about 0.001-2 moles, preferably about 0.005-0.7 mole, per mole of APAE, although said amount may vary depending on the kind of APAE. With an amine having insufficient basicity, such as triethylamine (pH value: 11.8), it is difficult to effect the racemization of APAE at a sufficient velocity. In the above racemization, the optically active APAE is used generally in an amount such that the concentration of said APAE in the racemization reaction system becomes about not less than 5 grams per liter, preferably about 10-500 grams per liter.

The racemization is preferably carried out in a homogenous system, as necessary in the presence of a reaction solvent. If inert to the APAE and strongly basic amine under racemization conditions, any reaction solvent may be used without restriction. Such reaction solvent thus includes, among others, ethers such as dipropyl ether, dibutyl ether, anisole, phenetole and diphenyl ether; hydrocarbons such as xylene, toluene, benzene, hexane and cyclohexane; phosphoric acid triesters such as triethyl phosphate and tributyl phosphate; nitriles such as propionitrile and benzonitrile; lower alcohols such as methyl alcohol, ethyl alcohol, propyl alcohol and butyl alcohol; carboxylic acid esters such as methyl acetate, ethyl acetate, propyl acetate, butyl acetate, methyl propionate, ethyl propionate, butyl propionate, methyl butyrate, ethyl butyrate, methyl valerate, ethyl valerate, methyl hexanoate, ethyl hexanoate, dimethyl adipate and diethyl phthalate; and amines such as triethylamine and dimethylaniline. These may be used either alone or as a mixture thereof. When an alcohol or a carboxylic acid ester is used as the reaction solvent, it is preferable to select the same such that said alcohol or the alcohol moiety of said carboxylic acid corresponds to the alcohol moiety constituting the APAE so that ester exchange between the reaction solvent and said APAE can be avoided. In recycling the APAE recovered from the reaction mixture given by the L-phenylalanine formation reaction according to the invention as a starting material after racemization thereof, it is not always necessary to separate said APAE from the organic layer in advance. Thus, in carrying out the L-phenylalanine formation reaction in the presence of water and a water-immiscible organic solvent, the use as the water-immiscible organic solvent of a nitrile containing not less than 3 carbon atoms, a carboxylic acid ester containing not less than 4 carbon atoms, an ether containing not less than 5 carbon atoms, an aromatic hydrocarbon containing not less than 6 carbon atoms, a phosphoric acid triester containing not less than 8 carbon atoms, a tertiary amine having at least one aromatic hydrocarbon residue substituent on the nitrogen atom, or the like, which is usable also in this racemization reaction, as mentioned above, makes it possible to submit the APAE-containing organic layer separated from the reaction mixture from the L-phenylalanine formation reaction step directly to racemization reaction.

When conducted in a water-free system, the racemization reaction gives favorable results. In cases where water is contained in the optically active APAE, strongly basic amine and/or reaction solvent to be used as a material for the racemization reaction, it is preferable to remove the water to a sufficient extent prior to racemization by subjecting the same to distillation, drying or the like. When water is present in the racemization reaction system, loss of APAE due to hydrolysis is unavoidable. Generally, the racemization reaction is carried out at a temperature within the range of about 40°-200° C., preferably within the range of about 60°-180° C., more preferably within the range of about 80°-160° C. At lower temperature, a prolonged period of time is required for the reaction whereas, at excessively high temperatures, unfavorable side reactions are ready to occur.

After the racemization reaction, the strongly basic amine in the reaction mixture is separated from the reaction mixture as necessary. When the strongly basic amine is a solid, insoluble amine such as an ion exchange resin, said amine can be separated by filtration. When the strongly basic amine is a liquid amine intimately mixed with the reaction mixture, such as DBU, DBN or TMG, said amine can be separated by subjecting the reaction mixture to distillation or extraction with water or by converting said amine to a carbonate, followed by crystallization of the carbonate from the reaction mixture. In causing precipitation of the strongly basic amine in the carbonate form, the reaction mixture containing the strongly basic amine is treated with water and carbon dioxide gas in the presence of a solvent in which said carbonate is insoluble or sparingly soluble. The solvent in which the strongly basic amine carbonate is insoluble or sparingly soluble is required to be inert to the APAE, strongly basic amine, water and carbon dioxide gas. Examples of such poor solvent are ethers such as dipropyl ether, dibutyl ether, anisole, phenetole and diphenyl ether; hydrocarbons such as xylene, toluene, benzene, hexane and cyclohexane; phosphoric acid triesters containing not less than 6 carbon atoms, such as triethyl phosphate and tributyl phosphate; nitriles containing not less than 4 carbon atoms, such as benzonitrile; and carboxylic acid esters such as methyl acetate, ethyl acetate, propyl acetate, butyl acetate, methyl propionate, ethyl propionate, butyl propionate, methyl butyrate, ethyl butyrate, methyl valerate, ethyl valerate, methyl hexanoate, ethyl hexanoate, dimethyl adipate and diethyl phthalate. Such poor solvent may be the racemization reaction solvent itself or such poor solvent may be added to the racemization reaction mixture. Water is used in an amount not less than the amount required for the strongly basic amine in the reaction mixture to form a carbonate salt. However, if water is used in large excess, the strongly basic amine in the carbonate form is dissolved in water, so that the precipitation yield decreases. Therefore, water is used generally in an amount within the range of about 1-10 equivalents, preferably within the range of about 1-3 equivalents, relative to the strongly basic amine. The amount of carbon dioxide gas is not critical if it is sufficient for the strongly basic amine in the reaction mixture to form a carbonate salt. The resulting precipitate of the carbonate-form strongly basic amine can easily be separated by filtration or the like procedure. Since the carbonate of the strongly basic amine is decomposed into the strongly basic amine, water and carbon dioxide gas upon heating, the strongly basic amine can be recovered from said carbonate salt very easily. It is preferable to conduct the procedure for decomposing the carbonate of the strongly basic amine under heating while removing the carbon dioxide and water from the system. As the technique for promoting removal of carbon dioxide, there may be mentioned, for example, the technique comprising conducting the decomposition under heating of the carbonate of strongly basic amine in an inert gas stream, such as a nitrogen gas stream, or under reduced pressure. For promoting water removal, the technique comprising conducting the decomposition under heating of the carbonate of strongly basic amine while distilling off the by-product water as an azeotrope with a solvent may be used, for instance.

Subjecting the racemization reaction mixture to the above strongly basic amine separation procedure gives a racemized APAE solution. The racemized APAE is isolated by subjecting said solution to recrystallization, distillation or the like separation procedure. When the racemized APAE is used as a part of the mixture of L-form of APAE and D-form of APAE which is the starting material for the L-phenylalanine formation reaction according to the invention, said racemized APAE may be either in the form of an APAE solution obtained after removal of the strongly basic amine from the above-mentioned racemization reaction mixture or in the form of an APAE crop isolated from said solution. Thus, when an organic solvent which is usable also for the L-phenylalanine formation reaction is used as the reaction solvent in the racemization step, it is possible to feed the racemized APAE solution obtained after removal of the strongly basic amine from the racemization reaction mixture to the L-phenylalanine formation reaction step.

The L-form of APAE to be used as the starting material for the L-phenylalanine formation reaction according to the invention can be produced in the form of a mixture with the corresponding D-form of APAE at low cost and in good yield by the following process found by the present inventors which starts with readily available commercial materials:

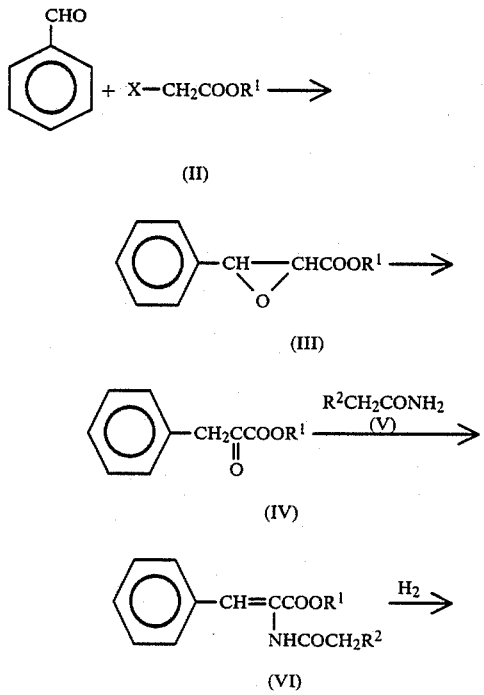

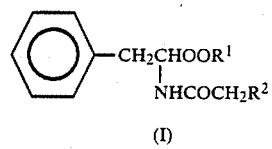

In the above formulas, X is a chlorine or bromine atom and $R^1$ and $R^2$ are as defined above.

Thus, a mixture of the L and D forms of an APAE can be advantageously produced by (i) reacting benzaldehyde with an α-haloacetic acid ester of the general formula (II) in the presence of potassium carbonate or potassium hydrogen carbonate and a polyoxyalkylene compound containing, on the average, at least 3 oxyethylene units per molecule while removing the resulting water from the reaction system to give a phenylglycidic acid ester of the general formula (III), (ii) isomerizing said phenylglycidic acid ester into a phenylpyruvic acid ester of the general formula (IV), (iii) reacting said phenylpyruvic acid ester with an acid amide of the general formula (V) in an amount of not more than 3 moles per mole of said phenylpyruvic acid ester in the presence of an acid with a pK value of not more than 3 at a temperature within the range of 100°–200° C. while removing the resulting water from the reaction system, to give an α-(acylamino)cinnamic acid ester of the general formula (VI), and (iv) hydrogenating said α-(acylamino)cinnamic acid ester.

As the α-haloacetic acid ester to be used in the phenylglycidic acid ester formation in the above step (i), mention may be made of methyl chloroacetate, ethyl chloroacetate, isopropyl chloroacetate, butyl chloroacetate, methyl bromoacetate, ethyl bromoacetate and the like. Said α-haloacetic acid ester is used generally in an amount of about 1–5 moles per mole of benzaldehyde. For increasing the benzaldehyde conversion to about 100 percent, the α-haloacetic acid ester is preferably used in an amount of not less than about 2 moles per mole of benzaldehyde.

The phenylglycidic acid ester formation reaction in the above step (i) is conducted while removing the by-product water from the reaction system. By doing so, the effect of potassium carbonate or potassium hydrogen carbonate used as the base is produced efficiently. Therefore, as mentioned later herein, the use of potassium carbonate or potassium hydrogen carbonate in a small amount within the range of about 1–2.3 gram equivalents per mole of benzaldehyde is sufficient. By conducting the reaction while removing the by-product water from the reaction system, the selectivity toward the phenylglycidic acid ester can be markedly improved since hydrolysis of the starting α-haloacetic acid ester and of the product phenylglycidic acid ester and self-condensation of the α-haloacetic acid ester can be inhibited. For removing the by-product water out of the system, the conventional method of distilling water out of the reaction system as used in the field of organic chemistry can be employed without any particular modification. In particular, the technique of distilling off water from the reaction system as an azeotrope is preferably employed. In distilling off the water as an azeotrope, the starting material α-haloacetic acid ester may be used also as the solvent for forming an azeotrope with the water. It is also possible to use an organic solvent which is stable and capable of forming an azeotrope with water under the reaction conditions but incapable of adversely affecting the reaction. Such organic solvent can be selected from among aliphatic, alicyclic, and aromatic hydrocarbons containing 5-15 carbon atoms, and monocarboxylic acid esters, dicarboxylic acid esters and ethers containing not more than 15 carbon atoms, and so forth. Suitable examples of the organic solvent are aliphatic hydrocarbons such as pentane, hexane, octane, decane, pentadecane and 2,4,6,8-tetramethylundecane; alicyclic hydrocarbons such as cyclohexane and methylcyclohexane; aromatic hydrocarbons such as benzene, toluene, xylene, ethylbenzene, cumene and diisopropylbenzene; monocarboxylic acid esters such as methyl acetate, ethyl acetate, isopropyl acetate, butyl acetate, amyl acetate, ethyl propionate, butyl propionate, isobutyl butyrate, methyl caprylate, isoamyl caprate and methyl benzoate; dicarboxylic acid esters such as diethyl malonate, dimethyl succinate, ethylene glycol diacetate and ethylene glycol dipropionate; and ethers such as diisopropyl ether, dibutyl ether, diheptyl ether, anisole, phenetole, ethylene glycol dimethyl ether, diethylene glycol diethyl ether, triethylene glycol butyl methyl ether, tetraethylene glycol dimethyl ether and diethylene glycol monomethyl ether monobutyl ester. Particularly preferred among these organic solvents from the viewpoints of stability in the reaction system, ready availability and so forth are aliphatic, alicyclic, and aromatic hydrocarbons containing 5-15 carbon atoms. When an organic solvent is used, the amount thereof is not critical provided that said amount is not less than the amount required for azeotrope formation with water. Generally, such solvent is used in an amount of about 0.1-5 volumes per volume of the total of the starting materials, namely benzaldehyde and α-haloacetic acid ester. It is not always necessary to subject the organic solvent to dehydration/drying treatment prior to use but a readily available commercial organic solvent intended for industrial use can be used as it is.

Particularly when potassium carbonate is used as the base, the reaction proceeds at high rate. The amount of potassium carbonate or potassium hydrogen carbonate is sufficient if it is within the range of about 1-2.3 gram equivalents per mole of benzaldehyde, and is preferably within the range of about 1.1-2.0 gram equivalents per mole of benzaldehyde. One mole of potassium hydrogen carbonate corresponds to one gram equivalent. Stoichiometrically, one gram equivalent of potassium carbonate or potassium hydrogen carbonate is required per mole of benzaldehyde in effecting the phenylglycidic acid formation reaction. For increasing the conversion of benzaldehyde to almost 100 percent, it is necessary to use potassium carbonate or potassium hydrogen carbonate in an amount of not less than 1 gram equivalent per mole of benzaldehyde. When potassium carbonate or potassium hydrogen carbonate is used in an amount within the range of about 1-2.3 gram equivalents per mole of benzaldehyde, the phenylglycidic acid ester can be formed in high selectivity and good yield and at the same time the residual amount of unreacted potassium carbonate or potassium hydrogen carbonate becomes small. The use of potassium carbonate or potassium hydrogen carbonate in an amount exceeding about 2.3 gram equivalents per mole of benzaldehyde cannot improve the selectivity toward phenylglycidic acid ester any longer but increases the amount of unreacted potassium carbonate or potassium hydrogen carbonate to no purpose. As will become apparent from the reference examples to appear later, the use, as the base, of other alkali metal compounds than potassium carbonate or potassium hydrogen carbonate, such as sodium carbonate, potassium hydroxide and sodium hydroxide, results in very low yields of phenylglycidic acid esters.

For effecting the reaction in the above step (i), it is necessary that a polyoxyalkylene compound containing, on the average, at least 3 oxyethylene units per molecule should be present in the reaction system. Such polyoxyalkylene compound may be either an acyclic polyoxyalkylene compound or a cyclic polyoxyalkylene compound.

As said acyclic polyoxyalkylene compound, there may be mentioned acyclic polyoxyalkylene compounds of the general formula

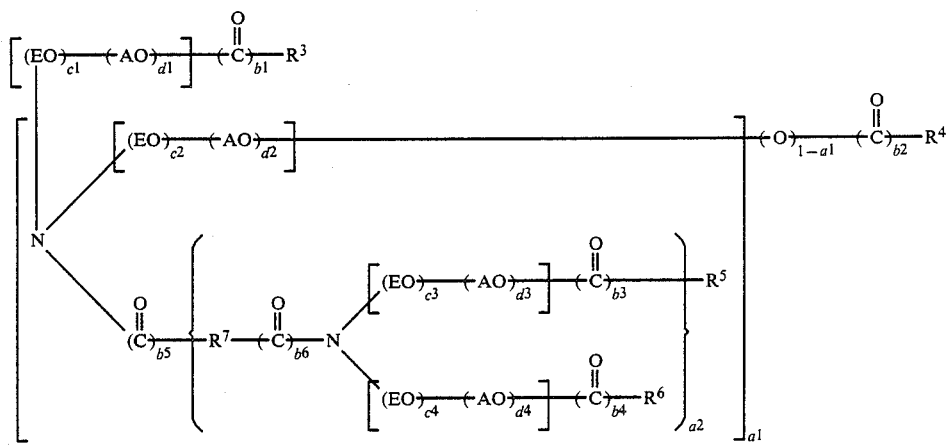

(VII)

Wherein $R^3$, $R^4$, $R^5$ and $R^6$ are each independently a hydrogen atom or an alkyl, cycloalkyl, aryl or aralkyl group containing 1-15 carbon atoms, which may optionally be substitued, $R^7$ is a straight-chain or branched-chain alkylene group containing 1-12 carbon atoms, E is an ethylene group, A is a propylene group [—CH(CH$_3$)CH$_2$—9 , $a^1$ and $a^2$ are each independently an integer of 0 or 1, $b^1$, $b^2$, $b^3$, $b^4$, $b^5$ and $b^6$ are each independently an integer of 0 or 1, $c^1$, $c^2$, $c^3$, $c^4$, $d^1$, $d^2$, $d^3$ and $d^4$ are each independently a number not less than 0 provided that the average value of ($c^1+c^2+c^3+c^4$) is within the range of 3-100, that the average value of ($d^1+d^2+d^3+d^4$) is within the range of 0-100 and that the average value of ($c^1+c^2+c^3+c^4$) is not less than the average value of $(d^1+d^2+d^3+d^4)$, and, in the $-[(OE)_{\overline{cm}}(OA)_{\overline{dm}}]-$ groups (m being 1, 2, 3 or 4), the $c^m$ —OE— units units and $d^m$ —OA— units may be arranged in any order. Referring to the above general formula (VII), the alkyl group that $R^3$, $R^4$, $R^5$ and $R^6$ each may independently represent is, for example, methyl, ethyl, propyl, isopropyl, butyl, isoamyl, hexyl, 1-ethylpentyl, 2-ethylhexyl, dodecyl, tetradecyl or pentadecyl; the cycloaklyl group is, for example, cyclohexyl or methylcyclohexyl; the aryl group is, for example, phenyl, tolyl, 2,4,6-trimethylphenyl or m-hexylphenyl; and the aralkyl group is, for example, benzyl. Such alkyl, cycloalkyl, aryl and aralkyl groups may optionally be substituted with one or more substituents such as halogen atoms, alkoxyl groups, hydroxyl group, hydrocarbyl group-substituted amino groups, acyl groups and alkoxycarbonyl groups. Examples of such substituted alkyl, cycloalkyl, aryl and aralkyl groups are trifluoromethyl, heptafluoropropyl, perfluorononyl, 4-chlorocyclohexyl, pentafluorophenyl, p-chlorophenyl, m-methoxyphenyl, p-methoxyphenyl, 2-hydroxypropyl, 2-(dimethylamino)ethyl, m-(diethylamino)phenyl, p-(dimethylamino)phenyl, m-methoxybenzyl, acetylmethyl, ethoxycarbonylmethyl and 1-(methoxycarbonyl)ethyl. The straight-chain or branched-chain alkylene group represented by $R^7$ is, for example, methylene, ethylene, trimethylene, propylene, tetramethylene, 1,2-dimethylethylene, hexamethylene, 3-methylpentamethylene, heptamethylene, octamethylene, nonamethylene, decamethylene, dodecamethylene, or 1-methylundecamethylene. For one single molecule, $c^1$, $c^2$, $c^3$, $c^4$, $d^1$, $d^2$, $d^3$, $d^4$, $c^1+c^2+c^3+c^4$ and $(d^1+d^2+d^3+d^4)$ each is an integer. However, in acyclic polyoxyalkylene compounds obtained by the conventional method of producing acyclic polyoxyalkylene compounds which is in general use, the values of $c^1$, $c^2$, $c^3$, $c^4$, $d^1$, $d^2$, $d^3$, $d^4$, $(c^1+c^2+c^3+c^4)$ and $(d^1+d^2+d^3+d^4)$ are, as a rule, not uniform among molecules. (Strictly, such compounds each is a mixture of acyclic polyoxyalkylene compounds.) In producing the phenylglycidic acid ester in the above step (i), such acyclic polyoxyalkylene compounds each may be used either without particular fractionation or after fractionation for narrowing the molecular weight distribution range to an adequate range. Accordingly, $c^1$, $c^2$, $c^3$, $c^4$, $d^1$, $d^2$, $d^3$, $d^4$, $(c^1+c^2+c^3+c^4)$ and $(d^1+d^2+d^3+d^4)$ in the above general formula (VII) each is not always an integer. More particularly, the acyclic polyoxyalkylene compounds of the above general formula (VII) include those compounds which have the following general formula (VII-1), (VII-2), (VII-3), (VII-4), (VII-5), (VII-6), (VII-7), (VII-8) or (VII-9):

(VII-1)

(VII-2)

(VII-3)

(VII-4)

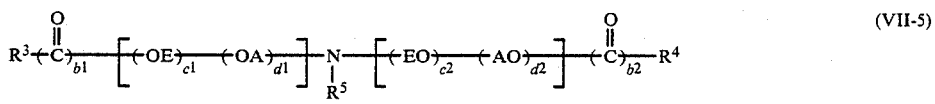

(VII-5)

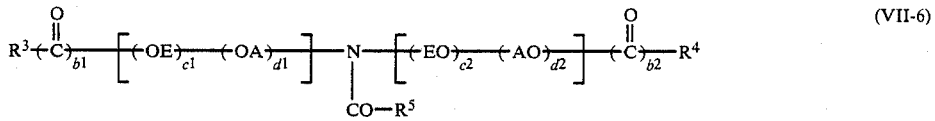

(VII-6)

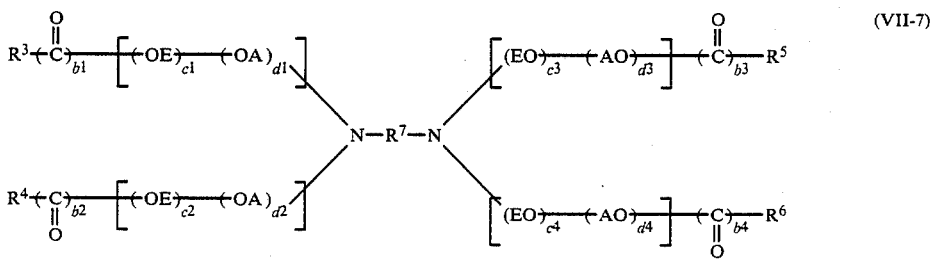

(VII-7)

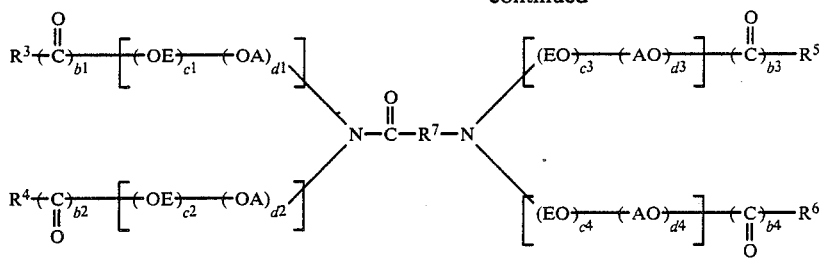

(VII-8)

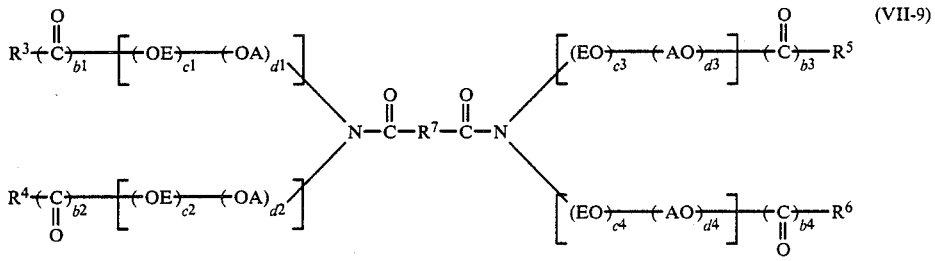

(VII-9)

In the above formulas, $R^3$, $R^4$, $R^5$, $R^6$, $R^7$, E, A, $b^1$, $b^2$, $b^3$, $b^4$, $c^1$, $c^2$, $c^3$, $c^4$, $d^1$, $d^2$, $d^3$, and $d^4$ are as defined above and, in each $[(OE)_{\overline{cm}}(OA)_{\overline{dm}}]$ (m standing for 1, 2, 3 or 4), the $c^m$ —OE— units and the $d^m$ —OA— units may be arranged in any order.

The compounds represented by general formula (VII-1) include polyethylene glycol, polyoxyethylene-polyoxypropylene glycol, and monoethers and diethers thereof. The compounds represented by general formula (VII-2) are mono-carboxylic acid esters or monoether mono-carboxylic acid esters of polyethylene glycol or polyoxyethylene-polyoxypropylene glycol. The compounds represented by general formula (VII-3) are dicarboxylic acid esters of polyethylene glycol or polyoxyethylene-polyoxypropylene glycol. The compounds represented by general formula (VII-4), (VII-5), (VII-6), (VII-7), (VII-8) or (VII-9) are nitrogen-containing compounds obtained by reacting an amine, acid amide, diaminoalkane, aminocarboxylic acid amide or dicarboxylic acid amide with ethylene oxide or with ethylene oxide and propylene oxide, followed, as the case may be, by etherification or esterification of the resulting product.

Examples of the cyclic polyoxyalkylene compound to be used in the phenylglycidic acid ester production in the above step (i) are crown ethers such as benzo-15-crown- 5, 18-crown-6, dicyclohexyl-18-crown-6, binaphtha-20-crown-6, 24-crown-8 and 30-crown-10; and cryptands such as cryptand[1,1,1], cryptand[2,1,1], cryptand[2,2,1], cryptand[2,2,2], cryptand[3,3,3], cryptand[2B,2B,2]and a compound of the formula

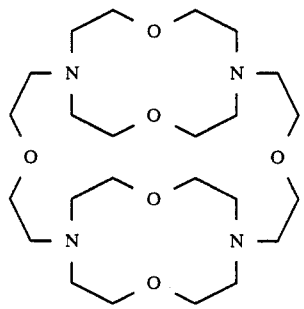

Among the above-mentioned polyoxyalkylene compounds, acyclic polyoxyalkylene compounds are preferred because of their ready availability. Furthermore, preferred from the viewpoints of reaction promotion, stability in the reaction system and so forth are polyethylene glycol containing, on the average, 5-50 oxyethylene units per molecule and dialkyl ethers thereof as well as polyoxyethylene-polyoxypropylene glycol of the formula

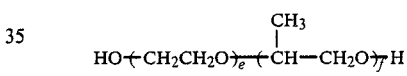

Wherein e is a number, on the average, within the range of 8-40 and is not less than f and (e+f) is a number, on the average, within the range of 10-70 and wherein the e oxyethylene units and f oxypropylene units may be arranged in any order, and dialkyl ethers thereof. Particularly preferred among them is polyethylene glycol containing, on the average, 10-50 oxyethylene units per molecule or the dimethyl ether thereof.

The amount of the above polyoxyalkylene compound to be used, which is suited for the intended purpose, may vary depending on the kind and amount each of the starting materials, namely benzaldehyde and a-haloacetic acid ester, the number of oxyethylene units in the polyoxyalkylene compound to be used, the presence or absence of a nitrogen atom or atoms therein, the kind of side chain therein and other factors, hence cannot be specified. Generally, however, the polyoxyalkylene compound is used in an amount such that its concentration in the liquid phase in the reaction system amounts to about 1-100 grams per liter. The use of the polyoxyalkylene compound in smaller amounts will fail to increase the rate of reaction to a satisfactory extent while, conversely, the use of the polyoxyalkylene compound in excess is uneconomical and moreover may, in some instances, adversely affect the procedure for product separation after the phenylglycidic acid ester formation reaction.

The reaction in the above step (i) is generally carried out within the temperature range of about 100°-200° C., preferably within the temperature range of 120°-160° C., although the reaction temperature which is adequate depends on the kind of the starting α-haloacetic acid ester. The reaction pressure is selected within the range within which the by-product water can be removed from the reaction system, while taking into consideration the reaction temperature, the boiling point each of benzaldehyde, α-haloacetic acid ester and organic solvent, and other factors. If the reaction pressure falls within said range, the reaction may be conducted at ordinary pressure, under increased pressure or under reduced pressure. The reaction system is preferably in an inert gas atmosphere, such as a nitrogen, argon, helium or carbon dioxide gas atmosphere, so that oxidation reactions generally caused by oxygen can be prevented from occurring. Since the reaction in the above step (i) is a reaction in a solid-liquid two-phase system, the reaction is preferably conducted with sufficient stirring for improving the contact between the solid and liquid phases. The phenylglycidic acid ester production reaction in the above step (i) may be carried out either continuously or batchwise.

In the above phenylglycidic acid ester production step (i), the desired phenylglycidic acid ester produced by the reaction can be separated from the reaction mixture by any appropriate method. Thus, for instance, the phenylglycidic acid ester can be recovered by removing the solid matter, such as potassium halide, from the reaction mixture by filtration and subjecting the filtrate to distillation or some other appropriate separation procedure. It is also possible to dissolve the solid matter by adding water to the reaction mixture, then recover the organic layer by phase separation, removing the organic solvent, unreacted starting materials, low-boiling by-products and so on from said organic layer by simple evaporation and isolate the phenylglycidic acid ester from the thus-obtained residue by fractional distillation, for instance. When the phenylglycidic acid ester is separated by distillation, the phenylglycidic acid ester may be accompanied by a byproduct α-halocinnamic acid ester. Since, however, said α-halocinnamic acid ester does not adversely affect the reactions in the above step (ii) and the subsequent steps, the phenylglycidic acid ester containing a certain amount of said α-halocinnamic acid ester can be used as the starting material for the isomerization reaction in the above step (ii).

In the above phenylglycidic acid ester isomerization step (ii), it is preferable for promoting the reaction that an acid, such as a protonic acid or a Lewis acid should be present in the reaction system. Said protonic acid includes, among others, sulfonic acids such as benzenesulfonic acid, p-toluenesulfonic acid, methanesulfonic acid, ethanesulfonic acid, trifluoromethanesulfonic acid and cyclohexanesulfonic acid; sulfonic acid type cation exchange resins such as Amberlyst 15 (Rohm and Haas Company), Amberlite IR-118 (Rohm and Haas Company), Diaion SKIA (Mitsubishi Chemical Industries, Limited) and Nafion 501 (E. I. du Pont de Nemours and Company); and inorganic acids such as phosphoric acid, sulfuric acid and hydrogen chloride. Said Lewis aid includes, among others, boron trifluoride [cf. e.g. Jouranal of the American Chemical Society, vol. 80 (1958), pp. 6386-6388]. Among the above acids, sulfonic acids and sulfonic acid type cation exchange resins are suitable since they give the desired phenylpyruvic acid ester in very high selectivity. From the viewpoints of catalyst activity, stability in reaction system, ease in handling and price, among others, benzenesulfonic acid, p-toluenesulfonic acid and Amberlyst 15, for instance, are particularly suitable. When a protonic acid is used as the acid, said protonic acid is generally used in an amount such that the concentration of the hydrogen atom involved in the dissociation of the protonic acid is within the range of about 1-300 milligram atoms per liter of the reaction mixture, although the optimum amount of said protonic acid may vary depending on the kind of said protonic acid, reaction temperature, etc., hence cannot be mentioned specifically. When a protonic acid is used, the reaction temperature is generally within the range of about 0°-150° C., preferably within the range of about 30°-120° C. although the optimum temperature may vary depending on the kind of the protonic acid employed and other factors. For inhibiting side reactions such as condensation, the phenylglycidic acid ester isomerization is preferably carried out in the presence of a solvent so that the total concentration of the phenylglycidic acid ester and phenylpyruvic acid ester in the reaction mixture can remain within the range of about 0.5-3 moles per liter. As said solvent, any solvent can be used if it does not adversely affect the phenylglycidic acid ester isomerization reaction. Examples of such solvent are aromatic hydrocarbons such as benzene, toluene and xylene; aliphatic hydrocarbons such as hexane and octane; alicyclic hydrocarbons such as cyclohexane; ethers such as dibutyl ether and anisole; and carboxylic acid esters such as methyl butyrate, ethyl butyrate and methyl benzoate. When boron trifluoride is used as the acid, the reaction is preferably conducted while maintaining boron trifluoride in a dissolved state in the presence of an organic solvent which will not adversely affect the catalyst activity of boron trifluoride. Usable solvents are, for example, aliphatic or alicyclic hydrocarbons such as pentane, hexane, cyclohexane and octane; aromatic hydrocarbons such as benzene; and halogenated hydrocarbons such as chloroform, carbon tetrachloride and dichlorobenzene. carbons such as chloroform and carbon tetrachloride. Boron trifluoride is used generally in an amount of not less than about 0.01 mole, preferably about 0.1-2 moles, per mole of the phenylglycidic acid ester. Boron trifluoride can be recovered from the reaction mixture by evaporation or the like and reused. The reaction is preferably carried out under increased pressure since boron trifluoride can then be allowed to remain in the liquid phase in the reaction system efficiently. The reaction temperature lies generally within the range of about 0°-100° C., preferably within the range of about 10°-80° C.

The desired phenylpyruvic acid ester can be separated by any appropriate technique from the reaction mixture obtained in the above phenylglycidic acid ester isomerization step (ii). Since, however, the phenylpyruvic acid ester is rather unstable to heat in a highly concentrated condition and readily undergoes side reactions such as self-condensation, it is preferable to use the reaction mixture resulting from the above phenylglycidic acid ester isomerization or the solution, containing the phenylpyruvic acid ester, obtained after removal of the acid from said reaction mixture by neutralization, washing with water and/or filtration, for instance, as the starting material for the α-(acylamino)cinnamic acid ester formation reaction in the above step (iii). In cases where an acid with a pKa value of not more than 3, such as mentioned later herein, is used as the acid in the above phenylglycidic acid ester isomerization, the reaction mixture obtained by said isomerization can be supplied to the α-(acylamino)cinnamic acid ester production step (iii) without removing the acid therefrom.

The above-mentioned acid amide of general formula (V) which is to be used as another starting material in the above step (iii) is, for example, acetamide, chloroacetamide, bromoacetamide, propionamide or butyramide. The acid amide is used in an amount of not more than 3 moles, preferably about 1.2–2.5 moles, more preferably about 1.2–2.0 moles, per mole of the phenylpyruvic acid ester. Whereas, stoichiometrically, the use of one mole of the acid amide per mole of the phenylpyruvic acid ester is sufficient, the use of said acid amide in excess relative to the phenylpyruvic acid ester tends to increase the rate of reaction. However, the use of the acid amide in an amount exceeding 3 moles per mole of the phenylpyruvic acid ester, said acid amide reacts not only with the carbonyl moiety in the α-position of the phenylpyruvic acid ester but also with the alkoxycarbonyl group portion, so that the formation of a byproduct c-(acylamino)cinnamic acid imide becomes significant, whereby the selectivity toward the α-(acylamino)cinnamic acid ester is reduced. Furthermore, for preventing self-condensation of the phenylpyruvic acid ester, it is preferable to maintain the concentration of the phenylpyruvic acid ester in the reaction system at a level not more than about 1.0 mole per liter of the reaction mixture. This concentration adjustment can be achieved, for example, by continuously or intermittenly adding the phenylpyruvic acid to the reaction mixture.

In the above step (iii), it is necessary that an acid with a pKa value of not more than 3 should be present in the reaction system. Said pKa value is the dissociation constant of the acid. The pKa values for various acids are described, for example, in "Kagaku Binran (Handbook of Chemistry)" Part I "Fundamentals" edited by the Chemical Society of Japan, revised second edition (1975), Maruzen Co., Ltd., Tokyo, pp. 994–998 and in R. C. Weast: "CRC Handbook of Chemistry and Physics", 62nd edition (1981-1982), CRC Press, Inc. (U.S.A.), pp. D-142 to D-144. Examples of such acid with pKa of not more than 3 are inorganic acids such as phosphoric acid [first dissociation constant (hereinafter referred to as "$pKa_1$"): 2.15], phosphorous acid ($pKa_1$ 2.00), pyrophosphoric acid ($pKa_1$ 1.7), sulfuric acid ($pKa_1$ ca. $-3$) and sulfurous acid ($pKa_1$ 1.76); sulfonic acids such as benzenesulfonic acid (pKa 0.70 , p-toluenesulfonic acid (pKa $-1.3$) and naphthalenesulfonic acid (pKa 0.57); carboxylic acids such as trichloroacetic acid (pKa 0.7), dichloroacetic acid (pKa 1.29), o-nitrobenzoic acid (pKa 2.170) and oxalic acid ($pKa_1$ 1.271); and sulfonic acid type cation exchange resins with pKa of not more than 3. Particularly preferred among these acids are sulfuric acid, sulfonic acids and sulfonic acid type cation exchange resins, among others. These acids are generally used in an amount such that the hydrogen atom involved in the dissociation of said acid is in a concentration generally within the range of about 0.5–100 milligram atoms per liter of the reaction mixture. When the α-(acylamino)cinnamic acid ester formation reaction is conducted in the absence of any acid or in the presence of an acid with a pKa value of more than 3 in the reaction system, the desired reaction hardly proceeds or, if proceeds, proceeds very slowly.

The α-(acylamino)cinnamic acid ester formation reaction is carried out generally within the temperature range of 100°–200° C., preferably within the temperature range of 110°–180° C., more preferably within the temperature range of 120°–160° C. To carry out the reaction at temperatures below 100° C. is not practical since the progress of reaction is slow. When the reaction is performed at temperatures higher than 200° C., self-condensation of the phenylpyruvic acid ester takes place to a significant extent and leads to a decreased selectivity toward the α-(acylamino)cinnamic acid ester.

It is necessary to conduct this reaction while removing the by-product water as it is formed. When the reaction is carried out without removing the by-product water from the reaction system, undesired reactions such as hydrolysis of the ester portion of the phenylpyruvic acid ester and of the α-(acylamino)cinnamic acid ester take place and reduce not only the selectivity toward α-(acylamino)cinnamic acid ester but also the rate of reaction. The by-product water removal from the reaction system can be effected by the method conventional in the field of organic chemistry which comprises carrying out reactions while distilling off the by-product water from the reaction system. In particular, it is preferable to employ the method comprising adding a solvent capable of forming an azeotrope with water to the reaction system and thus removing the water formed as the reaction proceeds from the reaction system in the form of an azeotrope with said solvent. Such measure enables quick removal of the by-product water from the reaction system and further enables removal of part of the heat of reaction as heat of vaporization, which in turn facilitates reaction temperature control. Examples of such solvent capable of forming an azeotrope with water include aromatic hydrocarbons such as benzene, toluene, xylene, mesitylene, ethylbenzene and cumene; ethers such as dibutyl ether, anisole, phenetole, ethylene glycol dimethyl ether and diethylene glycol dimethyl ether; carboxylic acid esters such as butyl acetate, ethyl butyrate, methyl benzoate and dimethyl malonate; and aliphatic hydrocarbons such as heptane and octane.

As regards the reaction pressure, any of the ordinary, reduced and increased modes can be optionally selected with reaction temperature, ease or difficulty in byproduct water removal, boiling points of the phenylpyruvic acid ester, acid amide and solvent employed, and other factors taken into consideration. The reaction can be conducted either batchwise or continuously.

After the α-(acylamino)cinnamic acid ester formation reaction, the product α-(acylamino)cinnamic acid ester can be isolated from the reaction mixture by, for example, subjecting the reaction mixture, as necessary after removal of the acid by neutralization, washing with water, filtration or the like, to distillation under reduced pressure or to distillation for removing the unreacted starting materials and the solvent, followed by recrystallization of the residue. The α-(acylamino)cinnamic acid ester to be used as the starting material in the aforementioned α-(acylamino)cinnamic acid ester hydrogenation step (iv) may be either in the form of an α-(acylamino)cinnamic acid ester-containing solution as obtained after removal of the acid from the reaction mixture resulting from the α-(acylamino)cinnamic acid ester formation reaction or in the form of an isolated crop of the α-(acylamino)cinnamic acid ester.

The hydrogenation of the α-(acylamino)cinnamic acid ester in the above-mentioned step (iv) is generally carried out in the presence of a hydrogenation catalyst. As such hydrogenation catalyst, any known hydrogenation catalyst for hydrogenating the ethylenic bond portion of olefinic compounds in general can be used. Examples of such catalyst thus include, among others, nickel catalysts such as Raney nickel and nickel-on-diatomaceous earth; and palladium catalysts such as palladium-on-carbon and palladium-on-alumina. It is possible, as mentioned hereinabove, to supply the phenylglycidic acid ester obtained in the above-mentioned step (i) in the form of a mixture of the same and the by-product α-halocinnamic acid ester to the above-mentioned step (ii), supply the phenylpyruvic acid ester obtained in the above step (ii) without isolation thereof to the above-mentioned step (iii) and supply the α-(acylamino)cinnamic acid ester obtained in the above step (iii) without isolation thereof to the above-mentioned step (iv). In this case, said α-halocinnamic acid ester generally undergoes no chemical changes in the above steps (ii) and (iii) and is supplied as it is to the above-mentioned α-(acylamino)cinnamic acid ester hydrogenation step (iv), where, in the α-(acylamino)cinnamic acid ester hydrogenation reaction system, it is converted to the corresponding 3-phenylpropionic acid ester. This conversion to the 3-phenylpropionic acid ester involves hydrogen halide generation. Therefore, the use of a palladium catalyst as said catalyst is preferred from the viewpoints of catalyst activity and catalyst life, among others. The hydrogenation catalyst is preferably used in a concentration of about 0.1–10 weight percent, more preferably in a concentration of about 0.5–5 weight percent, based on the reaction mixture. When the α-(acylamino)cinnamic acid ester obtained in the above step (iii) to be used as the starting material for this hydrogenation reaction is in the form of a mixture of the same and the α-halocinnamic acid ester such as mentioned above, a tertiary amine should preferably be present in the reaction system as an acceptor for the hydrogen halide formed. As such tertiary amine, tertiary amines used as hydrogen halide acceptors in general organic reactions can be used. Examples are pyridine, triethylamine, tributylamine and tricyclohexylamine.

The hydrogenation reaction is preferably carried out in the presence of a solvent. Examples of the solvent are aromatic hydrocarbons such as benzene, toluene, xylene, mesitylene, ethylbenzene and cumene; ethers such as dibutyl ether, anisole, phenetole, ethylene glycol dimethyl ether and diethylene glycol dimethyl ether; butyrate, methyl benzoate and dimethyl malonate; aliphatic hydrocarbons such as heptane and octane; lower alcohols such as methanol, ethanol and isopropyl alcohol; and cyclic ethers such as tetrahydrofuran and dioxane. The hydrogenation reaction is carried out in a hydrogen atmosphere where the hydrogen partial pressure is preferably within the range of about 1–150 kg/cm$^2$ (absolute), more preferably within the range of about 5–100 kg/cm$^2$ (absolute). Coexistence of a gas or gases inert to the hydrogenation reaction, such as nitrogen, helium, argon, methane and ethane, is by no means an obstacle to said reaction. The reaction temperature is preferably within the range of about 70°–180° C., more preferably within the range of about 80°–160° C.

The hydrogenation can be carried out in a per se known reactor such as a stirred tank reactor or a bubbling-column tower reactor. This hydrogenation reaction can be conducted either in the batchwise or in the continuous mode, with the continuous mode being preferred from the industrial standpoint. The hydrogenation reaction can also be carried out in two steps using two reactors in order that the conversion of the α-(acylamino)cinnamic acid ester can be increased. After removing the hydrogenation catalyst from the reaction mixture obtained in the above hydrogenation by an appropriate means such as filtration, precipitation or centrifugation, as necessary, a mixture of the L-form of APAE and D-form of APAE can be easily separated from said reaction mixture and purified, for example, by distillation, chromatography and/or recrystallization. The thus-obtained mixture of L-form of APAE and D-form of APAE is generally in the racemic modification form.

In accordance with the invention, L-phenylalanine having high optical purity can be produced in high yield from an APAE in L-form. In accordance with the invention, L-phenylalanine can be precipitated from the reaction mixture as crystals having high optical purity, so that the product L-phenylalanine can be recovered very easily without requiring particular separation and purification procedures which involve considerable utility consumption. Furthermore, in accordance with the invention, the enzyme activity can be maintained in the reaction system for a prolonged period of time and the enzyme recovered from the reaction mixture can be recycled and reused. In accordance with the invention, the residual APAE can be easily recovered from the reaction mixture and thus can be reused as a raw material.

L-phenylalanine, the product to be yielded by the method of the present invention, is an important substance in nutrition-promoting and pharmaceutical applications. It is also a useful material in synthesizing the artificial sweetener Aspartame (α-L-aspartyl-L-phenylalanine methyl ester).

Having generally described this invention, a further understanding can be obtained by reference to certain specific examples which are provided herein for purpose of illustration only and are not intended to be limitative of this invention unless otherwise specified.

EXAMPLE 1

(i) Production of methyl phenylglycidate

A one-liter three-necked flask equipped with thermometer, stirrer, dropping funnel and reflux condenser with azeotropic dehydration device was purged well with nitrogen gas and then charged, under nitrogen, with 53 g (0.5 mole) of benzaldehyde, 55 g (0.4 mole) of potassium carbonate, 8 g of polyethylene glycol having a number average molecular weight of 1,000 (the average number of oxyethylene units contained therein being 25) and 150 ml of o-xylene. The dropping funnel was charged with 163 g (1.5 moles) of methyl chloroacetate. Stirring was started at 800 r.p.m. and the three-necked flask was immersed in an oil bath and heated. When the inside temperature exceeded 100° C., dropwise addition of methyl chloroacetate from the dropping funnel was started and the reaction was carried out with heating under reflux of o-xylene. The addition of methyl chloroacetate was completed in 1 hour. Thereafter, the reaction was continued for 2 hours under the same conditions. During the reaction, the water formed was continuously removed from the reaction system by means of the azeotropic dehydration device. Gas chromatographic analysis revealed that the conversion of benzaldehyde after 3 hours of reaction was 83 percent, the selectivity toward methyl phenylglycidate 92 mole percent and the selectivity toward methyl α-chlorocinnamate 7 mole percent. After reaction, the reaction mixture was cooled and the stirring discontinued. No solid matter adhesion to the vessel wall was noted. To the reaction mixture was added 180 ml (i.e. 0.5 volume per total volume of the reaction mixture) of distilled water, followed by stirring at 500 r.p.m. for 15 minutes, whereby the solid matter was dissolved in water. From the resulting mixture composed of an aqueous layer and an organic layer, the organic layer was separated, the o-xylene, unreacted benzaldehyde and methyl chloroacetate were recovered by distillation, and the residue was subjected to distillation, whereby methyl phenylglycidate was obtained as a fraction boiling at 115°–118° C. at 5 mmHg. The distillate fraction contained 4 weight percent of methyl α-chlorocinnamate as an impurity. The above reaction and separation procedures were repeated to give a total of 116 g of the desired fraction.

(ii) Production of methyl phenylpyruvate

A one-liter three-necked flask equipped with thermometer, reflux condenser, stirrer and dropping funnel was purged with nitrogen gas and then charged, in a nitrogen gas stream, with 15 g of Amberlyst 15 (Rohm and Haas Company) and 410 ml of o-xylene, whereas the dropping funnel was charged with 93 g (0.5 mole) of the methyl phenylglycidate (containing 4 weight percent of methyl α-chlorocinnamate as an impurity) obtained in step (i) of Example 1. Stirring was started at 500 r.p.m., and the three-necked flask was immersed in an oil bath and heated. When the inside temperature exceeded 80° C., dropwise addition of methyl phenylglycidate from the dropping funnel was started, and the reaction was carried out at 100° C. The addition of methyl phenylglycidate was completed in 1 hour. Thereafter, the reaction was continued under the same conditions for 3 hours. Gas chromatographic analysis showed that the conversion of the methyl phenylglycidate charged was 100 percent at 4 hours after start of the reaction and the selectivity toward methyl phenylpyruvate 90 mole percent (yield of methyl phenylpyruvate 80 g). The methyl α-chlorocinnamate originally contained in the starting material methyl phenylglycidate remained unchanged. After reaction, the reaction mixture was cooled to room temperature and the Amberlyst 15 was filtered off in a nitrogen stream, whereupon an o-xylene solution containing 80 g of methyl phenylpyruvate was obtained.

(iii) Production of methyl α-acetamidocinnamate

A one-liter three-necked flask equipped with thermometer, stirrer, dropping funnel and reflux condenser with azeotropic dehydration device was purged well with nitrogen gas and then charged, under nitrogen, with 40 g (0.67 mole) of acetamide, 2.9 g (0.015 mole) of p-toluenesulfonic acid monohydrate, 100 ml of o-xylene and 50 ml of diethylene glycol dimethyl ether. The dropping funnel was charged with the whole amount (about 500 ml) of the o-xylene solution containing 80 g (0.45 mole) of methyl phenylpyruvate as obtained in step (ii) of Example 1. The flask contents were heated with stirring at a rate of 700 r.p.m. After the flask inside temperature exceeded 130° C., the o-xylene solution of methyl phenylpyruvate was added to the flask contents over 2 hours. After completion of the addition, the reaction was continued at a temperature of 144° C. under reflux of o-xylene for further 2 hours. During the reaction, the byproduct water was removed from the reaction system continuously by means of the azeotropic dehydration device. Gas chromatographic analysis showed that the conversion of methyl phenylpyruvate was 72 percent at 2 hours and 98 percent at 4 hours after start of the reaction. The selectivity toward methyl α-acetamidocinnamate on the consumed methyl phenylpyruvate basis was 90 mole percent at 4 hours after start of the reaction. (Yield of methyl α-acetamidocinnamate.87 g.) After completion of the reaction, the reaction mixture was cooled, 200 ml of distilled water was added thereto and the resultant mixture was stirred at a rate of 400 r.p.m. for 15 minutes. After removal of the aqueous layers by phase separation, a further 50-ml portion of distilled water was added to the organic layer, followed by stirring. These two washings removed the unreacted acetamide, the p-toluenesulfonic acid and diethylene glycol dimethyl ether from the reaction mixture. The above procedure gave about 630 ml of an o-xylene solution containing methyl α-acetamidocinnamate in a concentration of 0.63 mole per liter. The methyl α-chlorocinnamate contained in the o-xylene solution of methyl phenylpyruvate as submitted to the reaction was not involved in the reaction but remained in the o-xylene solution containing methyl α-acetamidocinnamate.

(iv) Production of N-acetyl-DL-phenylalanine methyl ester

A 500-ml stainless steel autoclave equipped with thermometer, pressure regulator and magnetic stirrer was purged well with hydrogen gas and then charged with a 300-ml portion of the o-xylene solution of methyl α-acetamidocinnamate as obtained in step (iii) of Example 1 [said portion containing 41 g (0.19 mole) of methyl α-acetamidocinnamate], 50 ml of methanol, 1 g of triethylamine and 1 g of a palladium-on-carbon catalyst (palladium content 5 weight percent; "Palladium Carbon" Nakarai Chemicals, Ltd.). Hydrogen gas was charged into the autoclave to a pressure of 30 kg/cm$^2$ (gauge) and the autoclave was immersed in an oil bath and heated to 100° C. (inside temperature). Stirring was then started at a rate of 800 r.p.m. and continued for 3 hours at the inside temperature of 100° C. while maintaining the pressure at 30 kg/cm$^2$ (gauge) by controlling the pressure regulator. Gas chromatographic analysis revealed that the conversion of methyl α-acetamidocinnamate at 3 hours after start of the reaction was 100 percent and the selectivity toward N-acetyl-DL-phenylalanine methyl ester 99 mole percent. After completion of the reaction, the autoclave was cooled and depressurized, and the palladium-on-carbon catalyst was filtered off from the reaction mixture. The o-xylene, methanol and other low-boiling fractions were distilled off from the filtrate under reduced pressure, and, further, the residue was distilled under reduced pressure to give 35 g of N-acetyl-DL-phenylalanine methyl ester as a fraction boiling at 170°–175° C./5 mmHg.

(v) Production of L-phenylalanine

A 2.0 g (9.0 millimole) portion of the N-acetyl-DL-phenylalanine methyl ester obtained in step (iv) of Example 1 was dissolved in a mixture of 100 ml of McIlvaine's buffer solution (pH 7) and 50 ml of 1.5 mM aqueous cobalt chloride solution. The solution was transferred to a 0.5-liter reaction vessel and 0.25 g of aminoacylase derived from a fungus belonging to the genus Aspergillus (Acylase "Amano" Amano Pharmaceutical Co., Ltd.) was added. The reaction was conducted with shaking at 37° C for 12 hours. Thereafter, the reaction mixture (pH 6.15) was analyzed by liquid chromatography. The residual N-acetylphenylalanine methyl ester was found to amount to 1.0 g (50 mole percent based on the N-acetyl-DL-phenylalanine methyl ester charged) and the yield of L-phenylalanine was 0.73 g (98 mole percent based on the N-acetyl-L-phenylalanine methyl ester supplied to the reaction system). The amount of N-acetylphenylalanine, a by-product, was trace. The aminoacylase was caused to aggregate by heating the reaction mixture and then removed by centrifugation. The solution obtained was extracted with three 25-ml portions of anisole, whereby the unhydrolyzed N-acetylphenylalanine methyl was recovered quantitatively. The extraction residue (aqueous layer) was concentrated under reduced pressure to give 15 ml of an aqueous solution. Treatment of this solution for crystallization gave 0.45 g of L-phenylalanine as crystals. The optical purity of the thus-obtained L-phenylalanine was 99 percent.

(vi) Racemization of N-acetylphenyl alanine methyl ester

The anisole solution (about 75 ml) containing 1.0 g of N-acetylphenylalanine methyl ester as obtained after extraction of the reaction mixture in step (v) of Example 1 was concentrated under reduced pressure while a trace amount of water dissolved in said solution was removed as an azeotrope with anisole. Thus was obtained 20 ml of an anisole solution containing 1.0 g of N-acetylphenylalanien methyl ester. Said N-acetylphenylalanine methyl ester had a specific rotation of $[\alpha]^{25}_D = -16.3°$ (c=1, methyl alcohol) and thus was a mixture of the D and L forms in which the D-form of N-acetylphenylalanine methyl ester was in excess. In the above 20-ml anisole solution containing 1.0 g of N-acetylphenylalanine methyl ester was dissolved 100 mg (0.65 millimoles) of DBU and the racemization reaction was carried out at 130° C. for 4 hours. Thereafter the reaction mixture was analyzed by liquid chromatography, which showed that the reaction mixture contained 0.98 g of N-acetylphenylalanine methyl ester (residual N-acetylphenylalanine methyl ester percentage: 98 percent).

The reaction mixture obtained was cooled to room temperature and 12 mg ( 0.67 millimole) of water was added thereto while carbon dioxide gas was blown thereinto with stirring. Bubbling with carbon dioxide gas and stirring were continued for further 10 minutes, and the resulting preceipitate was diltered off and washed with 10 ml of anisole. The filtrate and the washings were combined and the anisole was mostly distilled off under reduced prressure. Hexane (50 ml) was added to the residue and the mixture was allowed to stand overnight at about 5° C. The resultant precipitate was collected by filtration, washed with hexane and dried to give 0.78 g of N-acetylphenylalanine methyl ester as white crystals (recovery of N-acetylphenylalanine methyl ester: 80 precent). The N-acetylphenylalanine methyl ester thus obtained has a specific rotation of $[\alpha]^{25}_D = +0°$ (c=1, methyl alcohol) and thus proved to be N-acetyl-DL-phenylalanine methyl ester.

The above-mentioned precipitate formed upon blowing carbon dioxide gas in the reaction mixture was dried and then added to 10 ml of toluene, followed by heating under reflux in a nitrogen gas stream for 20 minutes, while removing the water which formed was removed from the reaction system using an azeotropic dehydration device. The toluene was then distilled off from the reaction mixture under reduced pressure. Titration of the residue with 1 N hydrochloric acid revealed that the residue contained 0.62 millimole of DBU (recovery of DBU: 95 percent).

(vii) Production of L-phenylalanine using, as part of starting material, N-acetyl-DL-phenylalanine methyl ester obtained by racemization reaction The enzymatic hydrolysis was carried out in the same manner as in step (v) of Example 1 except that 1.5 g of the N-acetyl-DL-phenylalanine methyl ester obtained by the hydrogenation in step (iv) of Example 1 and 0.5 g of the N-acetyl-DL-phenylalanine methyl ester obtained by the racemization in step (vi) of Example 1 were combinedly used in place of 2.0 g of the N-acetyl-DL-phenylalanine methyl ester obtained by the hydrogenation in step (iv) of Example 1. In the reaction mixture obtained, there remained 1.0 g of N-acetylphenylalanine methyl ester (50 mole percent based on the N-acetyl-DL-phenylalanine methyl ester charged) and the yield of L-phenylalanine was 0.73 g (98 mole percent based on the N-acetyl-L-phenylalanine methyl ester supplied to the reaction system). The L-phenylalanine isolated from said reaction mixture by crystallization had an optical purity of 99 percent.

EXAMPLE 2

(i) Production of methyl phenylglycidate

The reaction of step (i) of Example 1 was performed under same conditions as in said step except that the amount of potassium carbonate was changed from 55 g to 69 g (0.5 mole) and that 10 g of dimethyl ether of polyethylene glycol having a number average molecular weight of 1,000 (average number of oxyethylene units contained therein: 25) in place of the polyethylene glycol having a number average molecular weight of 1,000. The conversion of the benzaldehyde charged as determined at 3 hours after start of the reaction was 92 percent, with the selectivity toward methyl phenylglycidate calculated as 93 mole percent. The methyl phenylglycidate was separated from the reaction mixture in the same manner as in step (i) of Example 1. By repeating the above reaction and separation procedures, a total of 127 g of methyl phenylglycidate (containing 3 weight percent of methyl α-chlorocinnamate as an impurity) was prepared.

(ii) Production of methyl phenylpyruvate

The reaction of step (ii) of Example 1 was performed in the same manner as in said step except that 92 g (0.5 mole) of the methyl phenylglycidate as obtained in step (i) of Example 2 was used, that 5 g of Nafion 501 (E. I. du Pont de Nemours and Company) was used in lieu of 15 g of Amberlyst 15 and that the reaction temperature was changed from 100° C. to 50° C. At 4 hours after start of the reaction, the conversion of the methyl phenylglycidate charged was 100 percent and the selectivity toward methyl phenylpyruvate 92 mole percent. By removing the Nafion 501 in the same manner as in step (ii) of Example 1, an o-xylene solution containing 81 g of methyl phenylpyruvate was obtained.

(iii) Production of methyl α-acetamidocinnamate

The reaction of step (iii) of Example 1 was conducted in the same manner as in said step except that the o-xylene solution contianing 81 g of methyl phenylpyruvate as obtained in step (ii) of Example 2 was used, that acetamide was used in an amount of 47 g (0.08 mole)

and that 3.7 g (0.02 mole) of benzenesulfonic acid sesquihydrate was used in lieu of 2.9 g of p-toluenesulfonic acid monohydrate. At 4 hours after start of the reaction, the conversion of methyl phenylpyruvate was 99 percent and the selectivity toward methyl α-acetamidocinnamate was 88 mole percent based on the methyl phenylpyruvate consumed. Removing the unreacted acetamide and the benzenesulfonic acid in the same manner as in step (iii) of Example 1 gave an o-xylene solution containing methyl α-acetamidocinnamate in a concentration of 0.62 mole per liter.

(iv) Production of N-acetyl-DL-phenylalanine methyl ester

The hydrogenation procedure of step (iv) of Example 1 was followed using a 300-ml portion of the o-xylene solution containing methyl α-aetamidocinnamate as obtained in step (iii) of Example 2 (content of methyl α-acetamidocinnamate: 39 g) and, in place of 1 g of the palladium-on-carbon catalyst, 1.5 g of a palladium-on-alumina catalyst [pulverized "1% Pd on α-Al$_2$O$_3$ Spheres" (Nippon Engelhard, Ltd.); palladium content 1 weight percent] and changing the hydrogen pressure to 20 kg/cm$^2$ (gauge). At 5 hours after start of the reaction, the conversion of methyl α-acetamidocinnamate was 100 percent and the selectivity toward N-acetyl-DL-phenylalanine methyl ester 99 mole percent. After completion of the reaction, the separation and purification procedure of step (iv) of Example 1 was followed to give 33 g of N-acetyl-DL-phenylalanine methyl ester.

(v) Production of L-phenylalanine

The enzymatic hydrolysis of N-acetyl-DL-phenylalanine methyl ester was conducted under the same conditions as in step (v) of Example 1 except that 4 g of the N-acetyl-DL-phenylalanine methyl ester obtained in step (iv) of Example 2 was dissolved in a mixture of 100 ml of McIlvaine's buffer (pH 7), 50 ml of 1.5 mM aqueous cobalt chloride solution and 50 ml of methanol. When the reaction was completed, the reaction mixture had a pH of 6.70. Analysis by liquid chromatography showed that 2.20 g of N-acetylphenylalanine methyl ester remained unchanged (55 mole percent based on the N-acetyl-DL-phenylalanine methyl ester charged) and that the yield of L-phenylalanine was 1.30 g. After reaction, the methanol was distilled off from the reaction mixture under reduced pressure. The residue was heated to thereby cause aggregation of the aminoacylase and this was removed by centrifugation. Thereafter, the N-acetylphenylalanine methyl ester was quantitatively recovered by extraction with three 30-ml portions of p-xylene. The extraction residue solution (aqueous layer) was concentrated and subjected to crystallization treatment, which gave L-phenylalanine as crystals. The L-phenylalanine obtained had an optical purity of 99 percent.

(iv) Racemization of N-acetylphenylalanine methyl ester

The extract obtained in step (v) of Example 2 was concentrated under reduced pressure to give 40 ml of a p-xylene solution containing 2.2 g of N-acetylphenylalanine methyl ester. Said N-acetylphenylalanine methyl ester had a specific rotation of $[\alpha]_D^{25} = -14.5°$ (c=1, methyl alcohol) and thus was a mixture of the D and L forms of N-acetylphenylalanine methyl ester in which the D form was contained in excess. In a 20-ml portion of the 40 ml of p-xylene solution containing 2.2 g of N-acetylphenylalanine methyl ester was dissolved 100 mg of DBU and the racemization reaction was performed at 130° C. for 4 hours. When the reaction was completed, 1.07 g of N-acetylphenylalanine methyl ester was contained in the reaction mixture (residual percentage: 97 percent). Treatment of said reaction mixture in the same manner as in step (vi) of Example 1 gave 0.89 g of N-acetylphenylalanine methyl ester (83 percent recovery). The thus-obtained N-acetylphenylalanine methyl ester had a specific rotation of $[\alpha] = 0°$ (c=1, methyl alcohol) and thus was found to be N-acetyl-DL-phenylalanine methyl ester.

(vii) Production of L-phenylalanine using, as part of starting material, N-acetyl-DL-phenylalanine methyl ester obtained by racemization reaction The enzymatic hydrolysis was carried out in the same manner as in step (v) of Example 2 except that 3.5 g of the N-acetyl-DL-phenylalanine methyl ester obtained by the hydrogenation in step (iv) of Example 2 and 0.5 g of the N-acetyl-DL-phenylalanine methyl ester obtained by the racemization in step (vi) of Example 2 were used in admixture in place of 4 g of the N-acetyl-DL-phenylalanine methyl ester obtained by the hydrogenation in step (iv) of Example 2. The residual amount of N-acetylphenylalanine methyl ester in the reaction mixture obtained was 2.20 g (55 mole percent based on the N-acetyl-DL-phenylalanine methyl ester charged) and the yield of L-phenylalanine was 1.32 g (88 mole percent based on the N-acetyl-L-phenylalanine methyl ester supplied to the reaction system). The L-phenylalanine separated from said reaction mixture by a crystallization procedure had an optical purity of 99 percent.

EXAMPLE 3

(i) Production of methyl phenylglycidate

The reaction of step (i) of Example 1 was carried out in the same manner except that, instead of adding 163 g (1.5 moles) of methyl chloroacetate during reaction, the three-necked flask (reactor) was charged with 217 g (2.0 moles) of methyl chloroacetate prior to reaction and that the reaction was conducted in refluxing methyl chloroacetate without using o-xylene At 3 hours after start of the reaction, the conversion of benzaldehyde was 85 percent and the selectivity toward methyl phenylglycidate 90 mole percent. The methyl phenylglycidate was separated from the reaction mixture in the same manner as in step (i) of Example 1. The above reaction and separation procedures were repeated to give a total of 110 g of methyl phenylglycidate (containing 5 weight percent of methyl α-chlorocinnamate as an impurity).

(ii) Production of methyl phenylpyruvate

Using 94 g (0.5 mole) of the methyl phenylglycidate obtained in step (i) of Example 3, the isomerization reaction of step (ii) of Example 1 was conducted in the same manner except that toluene was used in place of o-xylene. At 4 hours after start of the reaction, the conversion of the methyl phenylglycidate charged was 100 percent and the selectivity toward methyl phenylpyruvate 91 mole percent. Removal of the Amberlyst 15 in the same manner as in step (ii) of Example 1 gave a toluene solution containing 81 g of methyl phenylpyruvate.

(iii) Production of methyl α-acetamidocinnamate

Using the toluene solution containing 81 g of methyl phenylpyruvate as obtained in step (ii) of Example 3, the reaction as performed in step (iii) of Example 1 was carried out while removing the byproduct water in the same manner except that p-toluenesulfonic acid monohydrate was used in an amount of 3.8 g (0.02 mole) and that the reaction was conducted in an autoclave at a temperature of 140° C. At 4 hours after start of the reaction, the conversion of methyl phenylpyruvate was 98 percent and the selectivity toward methyl α-acetamidocinnamate was 91 mole percent on the consumed methyl phenylpyruvate basis. The unreacted acetamide and the p-toluenesulfonic acid were removed from the reaction mixture in the same manner as in step (iii) of Example 1 to give a toluene solution containing methyl α-acetamidocinnamate in a concentration of 0.64 mole per liter.

(iv) Production of N-acetyl-DL-phenylalanine methyl ester

Using a 300-ml portion of the toluene solution of methyl α-acetamidocinnamate as obtained in step (iii) of Example 3 (said portion containing 42 g of methyl α-acetamidocinnamate), 5 g of a nickel-on-diatomaceous earth catalyst ("G-49B": Girdler Chemical Inc.) in lieu of 1 g of palladium-on-carbon catalyst, and 0.8 g of pyridine in lieu of 1 g of triethylamine, the hydrogenation reaction was carried out at a temperature of 150° C. for 5 hours under otherwise the same conditions in step (iv) of Example 1. At 5 hours after start of the reaction, the conversion of methyl α-acetamidocinnamate was 98 percent and the selectivity toward N-acetyl-DL-phenylalanine methyl ester 95 mole percent. After completion of the reaction, the reaction mixture was subjected to the same separation and purification procedure as in step (iv) of Example 1 to give 28 g of N-acetyl-DL-phenylalanine methyl ester.

(v) Production of L-phenylalanine

In a mixture of 10 ml of McIlvaine's buffer (pH 8) and 5 ml of 1.5 mM aqueous cobalt chloride solution was dissolved 25 mg of the same aminoacylase as used in step (v) of Example 1. The aqueous solution thus obtained was transferred to a 100-ml reaction vessel. A 1.0-g portion of the N-acetyl-DL-phenylalanine methyl ester obtained in step (iv) of Example 3 was dissolved in 5 ml of 3-heptanone and the solution was added to the aqueous solution in said reaction vessel. The two-layer mixture in the reaction vessel was shaken at 37° C. for 12 hours to thereby effect the enzymatic reaction. When the reaction was completed, the aqueous layer showed a pH of 4.95. Analysis of the aqueous and 3-heptanone layers by liquid chromatography and gas chromatography indicated that the aqueous layer contained 0.32 g of L-phenylalanine (42 mole percent based on the charged N-acetyl-DL-phenylalanine methyl ester), 0.037 g of N-acetyl-phenylalanine (4.0 mole percent based on the charged N-acetyl-DL-phenylalanine methyl ester), 0.055 g of methanol, 0.050 g of acetic acid and 0.09 g of N-acetylphenylalanine methyl ester whereas the 3-heptanone layer contained 0.44 g of N-acetylphenylalanine methyl ester, 0.013 g of methanol and trace amounts of L-phenylalanine, N-acetylphenylalanine and acetic acid.

The aqueous layer obtained was adjusted to pH 8 by adding 1 N aqueous sodium hydroxide. To this aqueous layer was added a solution of 1 g of the N-acetyl-DL-phenylalanine methyl ester obtained in step (iv) of Example 3 in 5 ml of 3-heptanone. The resultant two-layer-system mixture was shaken in the same manner as above at a temperature of 37° C. for 12 hours (repeated reaction run No. 1). When the reaction was completed, the pH of the aqueous layer was 5.50. Upon cooling the reaction mixture composed of the aqueous layer and 3-heptanone layer to room temperature, a supersaturation portion (0.11 g) of L-phenylalanine precipitated out on the aqueous layer side. Crystals of L-phenylalanine were separated by filtration. Then the filtrate was allowed to separate into the aqueous layer and 3-heptanone layer and the organic layer was removed. The aqueous layer was subjected to pH adjustment (pH 8) and reaction with N-acetyl-DL-phenylalanine methyl ester in 3-heptanone solution with shaking in the same manner as mentioned above and the resultant crystalline L-phenylalalnine precipitate (0.15 g) was collected by filtration (repeated run No. 2). By using the aminoacylase-containing aqueous layer of the filtrate in the above manner, the overall procedure comprising pH adjustment, reaction and L-phenylalanine separation was further repeated. The yields of L-phenylalanine in repeated runs No. 3, No. 4 and No. 5 were 0.16 g, 0.13 g and 0.12 g, respectively. The L-phenylalanine crystals obtained in the above repeated runs Nos. 1–5 (0.67 g in total) were combined and washed with methanol. The optical purity of the L-phenylalanine after washing (0.65 g) was found to be 98.9 percent.

(vi) Racemization of N-acetylphenylalanine methyl ester

The 3-pentanone layers separated from the respective reaction mixtures in the total of 6 reaction runs in step (v) of Example 3 were combined and low-boiling substances such as 3-heptanone were distilled off under reduced pressure. The residue, mainly N-acetylphenylalanine methyl ester, weighed 4.0 g and showed a specific rotation of $[\alpha]_D^{25} = -9.2°$ (c=1, methyl alcohol). It was thus found that said N-acetylphenylalanine methyl ester was a mixture of the D and L forms in which the D form was contained in excess. To the residue whose main component was N-acetylphenylalanine methyl ester, 25 ml of anisole and 0.25 g (2.0 millimoles) of DBN were added, and the reaction was carried out at 130° C. for 4 hours. When the reaction was completed, the residual amount of N-acetylphenylalanine methyl ester in the reaction mixture was 3.8 g (residual percentage: 95 percent). Said reaction mixture was treated in the same manner as in step (vi) of Example 1 to give 2.9 g of N-acetylphenylalanine methyl ester (recovery rate: 77 percent). The N-acetylphenylalanine methyl ester obtained showed a specific rotation of $[\alpha]_D^{25} = -0°$ (C=1, methyl alcohol) and was thus found to be N-acetyl-DL-phenylalanine methyl ester.

(vii) Production of L-phenylalanine using, as part of starting material, N-acetyl-DL-phenylalanine methyl ester obtained by racemization The enzymatic hydrolysis of step (v) of Example 3 was carried out in a total of 6 runs in the same manner as in said step except that, in each run, a mixture of 0.6 g of the N-acetyl-DL-phenylalanine methyl ester obtained by the hydrogenation in step (iv) of Example 3 and 0.4 g of the N-acetylphenylalanine methyl ester obtained in the racemization in step (vi) of Example 3 used in lieu of 1.0 g of the N-acetyl-DL-phenylalanine methyl ester obtained by the hydrogenation in step (iv) of Example 3. When the reaction mixtures obtained were combined, the total residual N-acetylphenylalanine methyl ester content therein was 4.2 g (70 mole percent based on the charged N-acetyl-DL-phenylalanine methyl ester) and the total L-phenylalanine yield was 1.3 g (58 mole percent based on the N-acetyl-L-phenylalanine supplied to the reaction system). The crystals of L-phenylalanine separated from said reaction mixture had an optical purity of 98.8 percent.

EXAMPLE 4

N-Acetyl-DL-phenylalanine methyl ester was prepared by following the procedures of steps (i), (ii), (iii) and (iv) of Example 1 and this was used as the starting material in the enzymatic hydrolysis mentioned below.

A 0.25-g portion of an aminoacylase derived from a fungus belonging to the genus Aspergillus (Aminoacylase: Tokyo Kasei kogyo Co., Ltd.) was dissolved in 5 ml of phosphate buffer (pH 7.0). To the solution were added 4 ml of 50 weight percent aqueous acrylamide solution, 4 ml of 4 weight percent aqueous solution of N,N'-methylenebisacrylamide, 2.5 ml of 5 weight percent aqueous solution of dimethylaminopropionitrile and 2.5 ml of 2.5 weight percent aqueous solution of potassium peroxodisulfate in that order, followed by stirring and allowing to stand for about 1 hour. The thus-obtained agar-like gel was cut to pieces (cubes, about 3×3×3 mm) and washed well with McIlvaine's buffer (pH 7.0). The enzymatic hydrolysis reaction was carried out in the same manner as in step (v) of Example 1 except that the polyacrylamide-immobilized aminoacylase prepared in the above manner was used as the aminoacylase. When the reaction was completed, the reaction mixture showed a pH of 6.20. Analysis by liquid chromatography indicated that the residual amount of N-acetylphenylalanine methyl ester was 1.0 g (50 mole percent based on the N-acetyl-DL-phenylalanine methyl ester charged) and the yield of L-phenylalanine 0.72 g (96 mole percent based on the N-acetyl-L-phenylalanine methyl ester supplied to the reaction system). The polyacrylamide-immobilized aminoacylase was filtered off from the reaction mixture obtained, and the L-phenylalanine was caused to crystalize out from the filtrate in the same manner as in step (v) of Example 1. The L-phenylalanine thus obtained had an optical purity of 99.0 percent.

The above filtrate was extracted with anisole and the extract was subjected to racemization in the same manner as in step (vi) of Example 1 to give 0.75 g of crystalline N-acetyl-DL-phenylalanine methyl ester. The above-mentioned enzymatic hydrolysis reaction was conducted in the same manner except that a mixture of 1.5 g of the N-acetyl-DL-phenylalanine methyl ester obtained by the above-mentioned hydrogenation and 0.5 g of the N-acetyl-DL-phenylalanine methyl ester obtained by the above racemization was used as the starting N-acetyl-DL-phenylalanine methyl ester. The yield of L-phenylalanine was 0.70 g and the L-phenylalanine separated as crystals from the reaction mixture had an optical purity of 98.9 percent.

EXAMPLE 5

Proceeding in the same manner as in steps (i), (ii), (iii), (iv) and (v) of Example 3 except that, in said step (v), trioctyl phosphate was used in lieu of 3-heptanone, there was obtained 720 mg of L-phenylalanine as crystals. Said L-phenylalanine had an optical purity of 99.0 percent.

EXAMPLE 6

Proceeding in the same manner as in steps (i), (ii), (iii), (iv) and (v) of Example 3 except that phenetole was used in place of 3-heptanone in said step (v), there was obtained 630 mg of L-phenylalanine as crystals. Said L-phenylalanine had an optical purity of 98.8 percent.

EXAMPLE 7

(i) Production of ethyl phenylglycidate

The corresponding reaction was conducted in the same manner as in step (i) of Example 1 except that 250 g (1.5 moles) of ethyl bromoacetate was used in lieu of methyl chloroacetate, that 88 g (1.0 mole) of potassium hydrogen carbonate was used in place of potassium carbonate, that 15 g of polyoxyethylenepolyoxypropylene glycol containing, on the average, 15 oxyethylene units and 10 oxypropylene units per molecule was used in lieu of polyethylene glycol having a number average molecular weight of 1,000 and that 150 ml of toluene was used in place of o-xylene. At 3 hours after start of the reaction, the conversion of the charged benzaldehyde amounted to 82 percent and the selectivity toward ethyl phenylglycidate was 88 mole percent. The ethyl phenylglycidate was separated from the reaction mixture in the same manner as in step (i) of Example 1. By repeating the above reaction and separation procedures, there was obtained a total of 118 g of ethyl phenylglycidate (containing 5 weight percent of ethyl α-bromocinnamate as an impurity).

(ii) Production of ethyl phenylpyruvate

The corresponding reaction was carried out in the same manner as in step (ii) of Example 1 except that 101 g (0.5 mole) of the ethyl phenylglycidate obtained in step (i) of Example 7 was used and that 5 g of p-toluenesulfonic acid monohydrate was used in lieu of Amberlyst 15. At 4 hours after start of the reaction, the conversion of ethyl phenylglycidate was 100 percent and the selectivity toward ethyl phenylpyruvate 90 mole percent (yield of ethyl phenylpyruvate: 86 g).

(iii) Production of ethyl α-(propionylamino)cinnamate

A one-liter three-necked flask equipped with thermometer, stirrer, dropping funnel and reflux condenser with azeotropic dehydration device was purged well with nitrogen gas and then charged with 49 g (0.67 mole) of propionamide and 100 ml of o-xylene in a nitrogen stream, while the dropping funnel was charged with the ethyl phenylpyruvate-containing reaction mixture obtained in step (ii) of Example 7 as it was without removing the p-toluenesulfonic acid. The mixture was stirred at a rate of 700 r.p.m. while raising the flask inside temperature. When said temperature exceeded 130° C., addition of the ethyl phenylpyruvate to the mixture in the flask was started. The addition was carried out portionwise over 2 hours. After completion of the addition, the reaction was continued for further 3 hours at 144° C. under reflux of o-xylene. During the reaction, the byproduct water formed with the progress of reaction was removed continuously from the reaction system by means of the azeotropic dehydration device. At 5 hours after start of the reaction, the conversion of ethyl phenylpyruvate was 99 percent and the selectivity toward ethyl α-(propionylamino)cinnamate was 86 mole percent based on the consumed ethyl phenylpyruvate. Removal of the unreacted propionamide and p-toluenesulfonic acid from the reaction mixture in the same manner as in step (iii) of Example 1 gave an o-xylene solution containing ethyl α-(propionylamino)cinnamate in a concentration of 0.60 mole per liter.

(iv) Production of N-propionyl-DL-phenylalanine ethyl ester

Using a 300-ml portion of the o-xylene solution of ethyl α-(propionylamino)cinnamate as obtained in step (iii) of Example 7 [said portion containing 44 g of ethyl α-(propionylamino)cinnamate] in place of the o-xylene solution of methyl α-acetamidocinnamate as used in step (iv) of Example 1, and 50 ml of ethanol in place of methanol, the hydrogenation reaction of step (iv) of Example 1 was performed in the same manner. At 3 hours after start of the reaction, the conversion of ethyl α-(propionylamino)cinnamate was 100 percent and the selectivity toward N-propionyl-DL-phenylalanine ethyl ester 99 mole percent. After completion of the reaction, the palladium-on-carbon catalyst was filtered off from the reaction mixture, and low-boiling substances such as o-xylene and ethanol were distilled off from the filtrate under reduced pressure. The residue was subjected to column chromatography for separation purposes. The subsequent purification by recrystallization gave 30 g of N-propionyl-DL-phenylalanine ethyl ester.

(v) Production of L-phenylalanine

Enzymatic hydrolysis of N-propionyl-DL-phenylalanine ethyl ester was carried out in the same manner as in step (v) of Example 1 except that a 4-g portion of the N-propionyl-DL-phenylalanine ethyl ester obtained in step (iv) of Example 7 was dissolved in a mixed solution composed of 100 ml of McIlvaine's buffer (pH 7), 50 ml of 1.5 mM aqueous cobalt chloride solution and 50 ml of ethanol. When the reaction was completed, the reaction mixture showed a pH of 6.80. Analysis by liquid chromatography indicated that said mixture contained 2.50 g of residual N-propionylphenylalanine ethyl ester (62 mole percent based on the charged N-propionyl-DL-phenylalanine ethyl ester) and that the yield of L-phenylalanine was 1.00 g. After completion of the reaction, the ethanol was distilled off from the reaction mixture under reduced pressure. By heating the residue, the aminoacylase was aggregated and then removed by centrifugation. The residual N-propionylphenylalanine ethyl ester was quantitatively recovered by extraction with three 30-ml portions of phenetole. The extraction residue (aqueous layer) was concentrated, followed by crystallization, which gave L-phenylalanine crystals. The L-phenylalanine thus obtained had an optical purity of 99 percent.

(vi) Racemization of N-propionylphenylalanine ethyl ester

The extract obtained in step (v) of Example 7 was concentrated under reduced pressure to give 40 ml of a phenetole solution containing 2.5 g of N-propionylphenylalanine ethyl ester. After dissolving 500 mg of TMG in the concentrated solution, racemization was effected at 130° C. for 6 hours. When the reaction was completed, the amount of residual N-propionylphenylalanine ethyl ester in the reaction mixture was 2.38 g (residual percentage: 95 percent). Treatment of said reaction mixture in the same manner as in step (vi) of Example 1 gave 1.90 g of N-propionylphenylalanine ethyl ester (80 percent recovery). Specific rotation measurement of the N-propionylphenylalanine ethyl ester thus obtained indicated that it was N-propionyl-DL-phenylalanine ethyl ester.

(vii) Production of L-phenylalanine using N-propionyl-DL-phenylalanine ethyl ester obtained by racemization as part of starting material The enzymatic hydrolysis reaction of step (v) of Example 7 was followed using a mixture of 2.5 g of the N-propionyl-DL-phenylalanine ethyl ester obtained by hydrogenation in step (iv) of Example 7 and 1.5 g of the N-propionyl-DL-phenylalanine ethyl ester obtained by racemization in step (vi) of Example 7 in place of 4 g of the N-propionyl-DL-phenylalanine ethyl ester obtained by hydrogenation in step (iv) of Example 7. The reaction mixture obtained contained 2.5 g of residual N-propionylphenylalanine ethyl ester (62 mole percent based on the charge N-propionyl-DL-phenylalanine ethyl ester) and the yield of L-phenylalanine was 1.0 g (75 mole percent based on the N-propionyl-L-phenylalanine ethyl ester supplied to the reaction system). The L-phenylalanine isolated from said reaction mixture as crystals had an optical purity of 98.8 percent.

EXAMPLE 8

(i) Production of butyl phenylglycidate

The reaction procedure of step (i) of Example 1 was followed using 226 g (1.5 moles) of butyl chloroacetate in lieu of methyl chloroacetate and using 10 g of polyethylene glycol having a number average molecular weight of 2,000 (average number of oxyethylene units contained: 45) in lieu of polyethylene glycol having a number average molecular weight of 1,000. At 3 hours after start of the reaction, the conversion of the charged benzaldehyde was 85 percent, the selectivity toward butyl phenylglycidate 90 mole percent and the selectivity toward butyl α-chlorocinnamate 8 mole percent. The same separation procedure as used in step (i) of Example 1 was applied to the reaction mixture to give 70 g of butyl phenylglycidate (containing 5 weight percent of butyl α-chlorocinnamate as an impurity). By repeating the above reaction and separation procedures, there was obtained a total of 140 g of butyl phenylglycidate (containing 5 weight percent of butyl α-chlorocinnamate as an impurity).

(ii) Production of butyl phenylpyruvate

The procedure of step (ii) of Example 1 was followed using 2 g (20 millimole) of sulfuric acid in lieu of Amberlyst 15, and 116 g (0.5 mole) of the butyl phenylglycidate obtained in step (i) of Example 8 (containing 5 weight percent of butyl α-chlorocinnamate) in lieu of methyl phenylglycidate. The total reaction time was prolonged to 5 hours. The conversion of butyl phenylglycidate was 98 percent and the selectivity toward butyl phenylpyruvate 88 mole percent (yield of butyl phenylpyruvate: 95 g).

(iii) Production of butyl α-acetamidocinnamate

Following the procedure of step (iii) of Example 1 but charging 1 g of sulfuric acid into the three-necked flask in lieu of p-toluenesulfonic acid monohydrate, and the whole o-xylene solution containing 95 g (0.43 mole) of butyl phenylpyruvate and sulfuric acid as obtained in step (ii) of Example 8 into the dropping funnel in place of methyl phenylpyruvate, the reaction was carried out in the same manner as in step (iii) of Example 1. The total reaction time was prolonged to 6 hours. The conversion of butyl phenylpyruvate was 97 percent and the selectivity toward butyl α-acetamidocinnamate 85 mole percent (yield of butyl α-acetamidocinnamate: 93 g). The reaction mixture was washed with water in the same manner as in step (iii) of Example 1 to give about 650 ml of an o-xylene solution containing butyl α-acetamidocinnamate in a concentration of about 0.55 mole per liter.

(iv) Production of N-acetyl-DL-phenylalanine butyl ester

Following the procedure of step (iv) of Example 1 but using a 300-ml portion of the o-xylene solution of butyl α-acetamidocinnamate as obtained in step (iii) of Example 8 in place of the o-xylene solution of methyl α-acetamidocinnamate, the hydrogenation reaction was carried out in the same manner as in said step (iv) of Example 1. The conversion of butyl α-acetamidocinnamate was 100 percent and the selectivity toward N-acetyl-DL-phenylalanine butyl ester 99 mole percent. The palladium-on-carbon catalyst was filtered off from the reaction mixture, the filtrate was concentrated under reduced pressure and the residue was purified by column chromatography to give 32 g of N-acetyl-DL-phenylalanine butyl ester.

(v) Production of L-phenylalanine

The procedure of step (v) of Example 1 was followed except that a further 25-ml portion of methanol was added to the reaction system, that 2 g (7.6 millimoles) of the N-acetyl-DL-phenylalanine butyl ester obtained in step (iv) of Example 8 was used in lieu of N-acetyl-DL-phenylalanine methyl ester, and that the aminoacylase was used in an amount of 0.40 g. The amount of residual N-acetylphenylalanine butyl ester was 1.0 g (50 mole percent based on the charged N-acetyl-DL-phenylalanine butyl ester) and the yield of L-phenylalanine was 0.61 g (98 mole percent based on the N-acetyl-L-phenylalanine butyl ester supplied to the reaction system).

EXAMPLE 9

(i) Production of methyl phenylglycidate

The procedure of step (i) of Example 1 was followed except that 12 g of polyethylene glycol having a number average molecular weight of 600 (average number of oxyethylene units contained: 13.6) was used in lieu of polyethylene glycol having a number average molecular weight of 1,000 and that the total reaction time was prolonged to 5 hours. At 5 hours after start of the reaction, the conversion of the charged benzaldehyde was 88 percent and the selectivity toward methyl phenylglycidate was 91 mole percent and that toward methyl α-chlorocinnamate 7 mole percent. The reaction mixture was subjected to the same isolation procedure as in step (i) of Example 1 to give 59 g of methyl phenylglycidate (containing 4 weight percent of methyl α-chlorocinnamate as an impurity). By repeating the above reaction and separation procedures, there was obtained a total of 119 g of methyl phenylglycidate (containing 4 weight percent of methyl α-chlorocinnamate as an impurity).

(ii) Production of methyl phenylpyruvate

A 2-liter three-necked flask equipped with stirrer, thermometer and dropping funnel was purged well with nitrogen gas and then charged, under nitrogen, with 1.5 liters of molecular sieve-dried benzene. Boron trifluoride gas (4 liters) was blown into the benzene to thereby cause dissolution of the boron trifluoride in the benzene. The dropping funnel was charged with a benzene solution (50 ml) containing 9.3 g (50 millimoles) of the methyl phenylglycidate (containing 4 weight percent of methyl α-chlorocinnamate as an impurity) obtained in step (i) of Example 9. The methyl phenylglycidate was dropped from the dropping funnel over 1 hour with stirring, during which the reaction temperature was maintained at a level not higher than 30° C. After completion of the dropping, the reaction was further continued for 1 hour under the same conditions. At 2 hours after start of the reaction, the conversion of methyl phenylglycidate was 95 percent and the selectivity toward methyl phenylpyruvate 85 mole percent. The reaction mixture was washed with a saturated aqueous sodium chloride solution and dried overnight over magnesium sulfate and, then, the solvent was distilled off under reduced pressure. The same reaction and treatment procedures were repeated further 5 times to give 42 g (0.23 mole) of crude methyl phenylpyruvate as a solid.

(iii) Production of methyl α-(hexanoylamino)cinnamate

A 500-ml three-necked flask equipped with thermometer, stirrer, dropping funnel and reflux condenser with an azeotropic dehydration device was purged well with nitrogen gas and then charged with 41 g (0.35 mole) of hexanamide, 20 g of Nafion 501 (E. I. du Pont de Nemours and Company) and 100 ml of o-xylene. The dropping funnel was charged with a solution (200 ml) prepared by dissolving the whole quantity of the methyl phenylpyruvate-containing solid obtained in step (ii) of Example 9 in o-xylene. While the flask contents were stirred at a rate of 500 r.p.m., the flask inside temperature was raised. When said inside temperature exceeded 130° C., addition of the methyl phenylpyruvate-containing o-xylene solution from the dropping funnel was started. This addition was conducted over 2 hours, after which the reaction was continued for 4 hours at a temperature of 144° C. under reflux of o-xylene. During the reaction, the water formed with the progress of reaction was continuously removed from the reaction system by means of the azeotropic dehydration device. At 6 hours after start of the reaction, the conversion of methyl phenylpyruvate was 94 percent and the selectivity toward methyl α-(hexanoylamino)cinnamate 83 mole percent. The reaction mixture obtained was cooled and the catalyst was filtered off to give about 320 ml of an o-xylene solution containing methyl α-(hexanoylamino)cinnamate in a concentration of 0.56 mole per liter.

(iv) Production of N-hexanoyl-DL-phenylalanine methyl ester

The hydrogenation reaction was carried out in the same manner as in step (iv) of Example 1 except that a 300-ml portion of the o-xylene solution of methyl α-(hexanoylamino)cinnamate as obtained in step (iii) of Example 9 was used in place of the o-xylene solution of methyl α-acetamidocinnamate. The conversion of methyl α-(hexanoylamino)cinnamate was 98 percent and the selectivity toward N-hexanoyl-DL-phenylalanine methyl ester 98 mole percent. The palladium-on-carbon catalyst was filtered off from the reaction mixture, the solvent was distilled off from the filtrate under reduced pressure, and the residue obtained was purified by column chromatography using a mixed solvent composed of benzene and methyl acetate as the developing solvent to give 33 g of N-hexanoyl-DL-phenylalanine methyl ester.

(v) Production of L-phenylalanine

Enzymatic hydrolysis was carried out in the same manner as in step (v) of Example 1 except that a further 25-ml of methanol was added to the reaction system, that 2 g (7.2 millimoles) of the N-hexanoyl-DL-phenylalanine methyl ester obtained in step (iv) of Example 9 was used in lieu of N-acetyl-DL-phenylalanine methyl ester and that the aminoacylase was used in an amount of 0.70 g. The residual amount of N-hexanoyl-phenylalanine methyl ester was 1.0 g (50 mole percent based on the charged N-hexanoyl-DL-phenylalanine methyl ester) and the yield of L-phenylalanine was 0.58 g (97 mole percent based on the N-hexanoyl-L-phenylalanine methyl ester supplied to the reaction system).

EXAMPLE 10

(i) Production of methyl phenylglycidate

The methyl phenylglycidate formation reaction was carried out in the same manner as in step (i) of Example 1 except that 12 g of polyoxyethylenepolyoxypropylene glycol containing, on the average, 10 oxyethylene units and 3 oxypropylene units per molecule was used in lieu of polyethylene glycol having a number average molecular weight of 1,000 and that the total reaction time was prolonged to 6 hours. At 6 hours after start of the reaction, the conversion of the charged benzaldehyde was 82 percent, and the selectivity toward methyl phenylglycidate was 89 mole percent and that toward methyl α-chlorocinnamate 8 mole percent. The same separation procedure as used in step (i) of Example 1 was applied to the reaction mixture to give 55 g of methyl phenylglycidate (containing 5 weight percent of methyl α-chlorocinnamate as an impurity). By repeating the above reaction and separation procedures, a total of 110 g of methyl phenylglycidate (containing 5 weight percent of methyl α-chlorocinnamate as an impurity) was obtained.

(ii) Production of methyl phenylpyruvate

Using 94 g (0.5 mole) of the methyl phenylgycidate obtained in step (i) of Example 10, the methyl phenylpyruvate formation reaction was carried out in the same manner as in step (ii) of Example 1 except that 3 g (30 millimoles) of orthophosphoric acid was used in place of Amberlyst 15 and that the total reaction time was prolonged to 6 hours. The conversion of methyl phenylglycidate was 99 percent and the selectivity toward methyl phenylpyruvate 85 mole percent (yield of methyl phenylpyruvate: 75 g).

(iii) Production of methyl α-acetamidocinnamate

The reaction of step (iii) of Example 1 was carried out in the same manner as in said step (iii) of Example 1 except that 2 g of orthophosphoric acid was charged into the three-necked flask in lieu of p-toluenesulfonic acid monohydrate, that the whole o-xylene solution containing 75 g (0.42 mole) of methyl phenylpyruvate together with orthophosphoric acid as obtained as a reaction mixture in step (ii) of Example 10 was charged as the starting material into the dropping funnel and that the total reaction time was prolonged to 7 hours. The conversion of methyl phenylpyruvate was 96 percent and the selectivity toward methyl α-acetamidocinnamate 83 mole percent (yield of methyl α-acetamidocinnamate: 73 g). The reaction mixture was subjected to the same water-washing treatment as in step (iii) of Example 1 to give about 620 ml of an o-xylene solution containing methyl α-acetamidocinnamate in a concentration of about 0.53 mole per liter.

(iv) Production of N-acetyl-DL-phenylalanine methyl ester

The hydrogenation procedure of step (iv) of Example 1 was followed using a 300-ml portion of the o-xylene solution of methyl α-acetamidocinnamate as obtained in step (iii) of Example 10. The conversion of methyl α-acetamidocinnamate was 99 percent and the selectivity toward N-acetyl-DL-phenylalanine methyl ester 99 mole percent. The palladium-on-carbon catalyst was filtered off from the reaction mixture, the filtrate was concentrated under reduced pressure and the residue was purified by column chromatography to give 26 g of N-acetyl-DL-phenylalanine methyl ester.

(v) Production of L-phenylalanine

The N-acetyl-DL-phenylalanine methyl ester obtained in step (iv) of Example 10 was enzymatically hydrolyzed in the same manner as in step (v) of Example 1. The residual quantity of N-acetylphenylalanine methyl ester was 1.0 g (50 mole percent based on the charged N-acetyl-DL-phenylalanine methyl ester) and the yield of L-phenylalanine 0.72 g (96 mole percent based on the N-acetyl-L-phenylalanine methyl ester supplied to the reaction system).

EXAMPLE 11

(i) Production of methyl phenylglycidate

The procedure of step (i) of Example 1 was followed except that 12 g of polyoxyethylenepolyoxypropylene glycol containing, on the average, 35 oxyethylene units and 20 oxypropylene units per molecule was used in lieu of polyethylene glycol having a number average molecular weight of 1,000 and that the total reaction time was prolonged to 5 hours. At 5 hours after start of the reaction, the conversion of the charged benzaldehyde was 83 percent, and the selectivity toward methyl phenylglycidate was 88 mole percent and that toward methyl α-chlorocinnamate 9 mole percent. The same separation procedure as used in step (i) of Example 1 was applied to the reaction mixture to give 54 g of methyl phenylglycidate (containing 5 weight percent of methyl α-chlorocinnamate as an impurity). By repeating the above reaction and separation procedures, a total of 107 g of methyl phenylglycidate (containing 5 weight percent of methyl α-chlorocinnamate) was prepared.

(ii) Production of methyl phenylpyruvate

A one-liter glass-made autoclave equipped with a magnetic stirrer was purged well with nitrogen gas, then charged with 94 g (0.5 mole) of the methyl phenylglycidate obtained in step (i) of Example 11 and a solution (420 ml) prepared by dissolving about 2 g of hydrogen chloride gas in diethyl ether dried in advance on metallic sodium, and tightly closed, and the reaction was carried out for 24 hours in a water bath maintained at 50° C. At 24 hours after start of the reaction, the conversion of methyl phenylglycidate was 95 percent and the selectivity toward methyl phenylpyruvate 82 mole percent. After completion of the reaction, the reaction mixture was neutralized by washing with 100 ml of a saturated aqueous solution of sodium hydrogen carbonate. The ether layer was separated and dried over anhydrous sodium sulfate, and the ether was then distilled off to give a solid containing 69 g of methyl phenylpyruvate.

(iii) Production of methyl α-acetamidocinnamate

The solid containing 69 g of methyl phenylpyruvate as obtained in step (ii) of Example 11 was dissolved in o-xylene. Using this solution (500 ml), the reaction procedure of step (iii) of Example 1 was followed in the same manner except that 4 g of trichloroacetic acid was used in place of p-toluenesulfonic acid monohydrate and that the total reaction time was prolonged to 7 hours. The conversion of methyl phenylpyruvate was 97 percent and the selectivity toward methyl α-acetamidocinnamate 84 mole percent (yield of methyl α-acetamidocinnamate: 69 g). The reaction mixture was subjected to the same water-washing treatment to give about 600 ml of an o-xylene solution containing methyl α-acetamidocinnamate in a concentration of about 0.52 mole per liter.

(iv) Production of N-acetyl-DL-phenylalanine methyl ester

A 300-ml portion of the o-xylene solution of methyl α-acetamidocinnamate as obtained in step (iii) of Example 11 was subjected to hydrogenation in the same manner as in step (iv) of Example 1. The conversion of methyl α-acetamidocinnamate was 99 percent and the selectivity toward N-acetyl-DL-phenylalanine methyl ester 99 mole percent. The palladium-on-carbon catalyst was filtered off from the reaction mixture, low-boiling substances were distilled off from the filtrate, and the residue obtained was distilled under reduced pressure to give 27 g of N-acetyl-DL-phenylalanine methyl ester.

(v) Production of L-phenylalanine

The N-acetyl-DL-phenylalanine methyl ester obtained in step (iv) of Example 11 was subjected to enzymatic hydrolysis in the same manner as in step (v) of Example 1. The residual amount of N-acetylphenylalanine methyl ester was 1.0 g (50 mole percent based on the charged N-acetyl-DL-phenylalanine methyl ester) and the yield of L-phenylalanine was 0.72 g (96 mole percent based on the N-acetyl-L-phenylalanine methyl ester supplied to the reaction system).

EXAMPLE 12

(i) Production of methyl α-[(chloroacetyl)amino]cinnamate

Using an about 500-ml portion of an o-xylene solution of methyl phenylpyruvate as obtained in the same manner as in steps (i) and (ii) of Example 1 (said portion containing 80 g of methyl phenylpyruvate) and using 63 g (0.67 mole) of chloroacetamide in lieu of acetamide, the procedure of step (iii) of Example 1 was followed. The total reaction time was prolonged to 7 hours. The conversion of methyl phenylpyruvate was 95 percent and the selectivity toward methyl α-[(chloroacetyl)amino]cinnamate 80 mole percent, the yield of methyl α-[(chloroacetyl)amino]cinnamate being 86 g. The reaction mixture was subjected to water-washing treatment in the same manner as in step (iii) of Example 1 to give about 610 ml of an o-xylene solution containing methyl α-[(chloroacetyl)amino]cinnamate in a concentration of about 0.55 mole per liter.

(ii) Production of N-(chloroacetyl)-DL-phenylalanine methyl ester

A 300-ml portion of the o-xylene solution of methyl α-[(chloroacetyl)amino]cinnamate as obtained in step (i) of Example 12 was subjected to hydrogenation in the same manner as in step (iv) of Example 1. The conversion of methyl α-[(chloroacetyl)amino]cinnamate was 98 percent, and the selectivity toward N-(chloroacetyl)-DL-phenylalanine methyl ester was 70 mole percent based on the consumed methyl α-[(chloroacetyl)amino]cinnamate and that toward N-acetyl-DL-phenylalanine methyl ester 28 mole percent on the same basis. After completion of the reaction, the reaction mixture was concentrated under reduced pressure and the residual concentrate purified by column chromatography to give 21 g of 95 weight percent pure N-(chloroacetyl)-DL-phenylalanine methyl ester (containing 5 weight percent of N-acetyl-DL-phenylalanine methyl ester as an impurity).

(iii) Production of L-phenylalanine

A 2-g (7.4-millimole) portion of the mixture of 95 weight percent of N-(chloroacetyl)-DL-phenylalanine methyl ester and 5 weight percent of N-acetyl-DL-phenylalanine methyl ester as obtained in step (ii) of Example 12 was used in place of the N-acetyl-DL-phenylalanine methyl ester used in step (v) of Example 1 and thus subjected to enzymatic hydrolysis in the same manner as in step (v) of Example 1 except that an additional 15 ml of methanol was further added to the reaction system. In the reaction mixture obtained, there remained a total of 1.0 g of N-(chloroacetyl)phenylalanine methyl ester and N-acetylphenylalanine methyl ester [50 mole percent based on the total amount of N-(chloroacetyl)-DL-phenylalanine methyl ester and N-acetyl-DL-phenylalanine methyl ester supplied to the reaction system] and the yield of L-phenylalanine was 0.63 g [97 mole percent based on the total amount of N-(chloroacetyl)-L-phenylalanine methyl ester and N-acetyl-L-phenylalanine methyl ester].

REFERENCE EXAMPLES 1-3

The reaction and reaction mixture treatment procedures of steps (i), (ii), (iii), (iv), (v) and (vi) of Example 1 were followed except that, in step (vi), the amines indicated below in Table 1 were respectively used in an amount of 0.65 millimole. The results thus obtained in racemization of N-acetylphenylalanine methyl ester are shown in Table 1.

TABLE 1

| REFERENCE EXAMPLE | Amine | | Yield in racemization of N—acetylphenylalanine methyl ester (%) |
|---|---|---|---|
| | Species | pH of 0.1 mole/liter aqueous solution at 25° C. | |
| 1 | Imidazole | 10.1 | 2 |
| 2 | Triethylenediamine | 11.0 | 1 |

TABLE 1-continued

| REFERENCE EXAMPLE | Amine | | Yield in racemization of N—acetylphenylalanine methyl ester (%) |
|---|---|---|---|
| | Species | pH of 0.1 mole/liter aqueous solution at 25° C. | |
| 3 | Triethylamine | 11.8 | 0 Note (1) |

Note (1): The racemization reaction was conducted in an autoclave under pressure to thereby prevent the evaporation of triethylamine from the liquid phase of the reaction system.

REFERENCE EXAMPLE 4

The methyl phenylglycidate formation reaction was carried out in the same reaction apparatus and in the same manner as in step (i) of Example 1 except that a reflux condenser without any azeotropic dehydration device was used in lieu of the reflux condenser with azeotropic dehydration device and that, accordingly, the byproduct water removal from the reaction system was not effected. At 3 hours after start of the reaction, the conversion of benzaldehyde was 58 percent and the selectivity toward methyl phenylglycidate 79 mole percent. During the reaction, the reaction mixture was withdrawn in trace amounts and analyzed by gas chromatography. It was noted that at about 2 hours after start of the reaction and thereafter, the rate of reaction quickly decreased. After completion of the reaction, the aqueous layer obtained after washing of each reaction mixture with water was acidified with dilute hydrochloric acid and analyzed by gas chromatography, which indicated that the yields of chloroacetic acid, phenylglycidic acid, methanol, etc. were significantly great as compared with the case of step (i) of Example 1.

REFERENCE EXAMPLE 5

The methyl phenylglycidate formation reaction was carried out under the same conditions as used in step (i) of Example 1 except that 8 g of diethylene glycol dimethyl ether was used in place of 8 g of polyethylene glycol having a number average molecular weight of 1,000. At 3 hours after start of the reaction, the conversion of benzaldehyde was 28 percent.

REFERENCE EXAMPLE 6

The methyl phenylglycidate formation reaction was carried out under the same conditions as used in step (i) of Example 1 except that 8 g of polyethylene glycol dimethyl ether having a number average molecular weight of 1,000 (average number of oxyethylene units contained: 25) was used in lieu of 8 g of dimethyl ether of polyethylene glycol having a number average molecular weight 1,000 and that 34 g (0.61 mole) of potassium hydroxide was used in place of 55 g of potassium carbonate. At 3 hours after start of the reaction, the selectivity toward methyl phenylglycidate was as small as 18 mole percent although the conversion of benzaldehyde was 88 percent. Formation of such byproducts as benzyl alcohol, benzoic acid and methyl benzoyloxyacetate in large amounts was noted.

REFERENCE EXAMPLE 7

The methyl phenylglycidate formation reaction was carried out under the same conditions as used in step (i) of Example 1 except that 42.4 g (0.4 mole) of sodium carbonate was used in lieu of 55 g (0.4 mole) of potassium carbonate. At 3 hours after start of the reaction, the conversion of benzaldehyde was 16 percent.

REFERENCE EXAMPLE 8

A 500-ml round bottom flask was charged with 3.0 g (0.018 mole) of phenylpyruvic acid and 3.0 g (0.051 mole) of acetamide. After connection of an air condenser to the flask top, the pressure within the flask was reduced to 10–15 mmHg (absolute) using an aspirator. The round bottom flask was immersed in an oil bath, then heating was started with stirring, and the reaction was conducted at an oil bath temperature of 120° C. under the above reduced pressure for 4 hours. After completion of the reaction, the reaction mixture obtained was analyzed by high speed liquid chromatography, whereupon it was found that the conversion of phenylpyruvic acid was 94 percent and the selectivity toward α-acetamidocinnamic acid 57 mole percent based on the converted phenylpyruvic acid, with formation of various phenylpyruvic acid-derived condensation products as byproducts.

REFERENCE EXAMPLE 9

The reaction procedure of Reference Example 8 was followed using 3.2 g (0.018 mole) of methyl phenylpyruvate in lieu of 3 g of phenylpyruvic acid. After completion of the reaction, the reaction mixture obtained was analyzed by gas chromatography. It was indicated that the methyl phenylpyruvate and acetamide remained quantitatively.

REFERENCE EXAMPLES 10–14

The procedures of steps (i), (ii) and (iii) of Example 1 were followed except that, in step (iii), the acetamides specified in Table 2 were respectively used and that, in place of p-toluenesulfonic acid monohydrate, the acids indicated in Table 2 were used in the respective amounts given in Table 2. The conversion of methyl phenylpyruvate and the selectivity toward methyl α-acetamidocinnamate on the converted methyl phenylpyruvate basis as determined for each run at 4 hours after start of the reaction between methyl phenylpyruvate and acetamide are shown in Table 2.

TABLE 2

| REFERENCE EXAMPLE | Amount of acetamide (moles) | Acid | | Results | |
|---|---|---|---|---|---|
| | | Species | Amount (mole) | Conversion (%) | Selectivity (mole %) |
| 10 | 1.80 | p-Toluenesulfonic acid monohydrate | 0.015 | 98 | 73*[1] |
| 11*[2] | 0.67 | p-Toluenesulfonic acid monohydrate | 0.015 | 100 | 59*[3] |
| 12*[4] | 0.67 | p-Toluenesulfonic acid monohydrate | 0.015 | 95 | 52*[5] |
| 13 | 0.67 | Formic acid (pKa 3.75) | 0.02 | 25 | 86 |
| 14 | 0.67 | Terephthalic acid | 0.02 | 29 | 85 |

TABLE 2-continued

| REFERENCE EXAMPLE | Amount of acetamide (moles) | Acid Species | Amount (mole) | Results Conversion (%) | Selectivity (mole %) |
|---|---|---|---|---|---|
| | | (pKa 3.51) | | | |

Note (1): Formation of byproduct α-acetamido-N—acetoxy-3-phenyl-2-propenamide was significant.
Note (2): The reaction between methyl phenylpyruvate and acetamide was performed at a temperature of 210° C. under increased pressure.
Note (3): Byproducts such as methyl phenylpyruvate dimer were noted in large amounts.
Note (4): In reacting methyl phenylpyruvate with acetamide, the whole amount of methyl phenylpyruvate was added to the reaction system at the start of reaction and the byproduct water formed during the reaction was not removed from the reaction system.
Note (5): Formation of byproducts such as α-acetamidocinnamic acid, phenylacetaldehyde condensation products and phenylpyruvic acid was noted.

REFERENCE EXAMPLE 15

By following the procedure of steps (i) and (ii) of Example 9, a solid containing 42 g (0.23 mole) of methyl phenylpyruvate was prepared. The methyl phenylpyruvate was reacted with hexanamide in the same manner as in step (iii) of Example 9 except that 100 ml of benzene was charged into the three-necked flask in place of 100 ml of o-xylene, that a solution (200 ml) prepared by dissolving the above methyl phenylpyruvate-containing solid in benzene was charged into the dropping funnel in lieu of the o-xylene solution of the phenylpyruvate-containing solid obtained in step (ii) of Example 9, that the addition of the benzene solution of methyl phenylpyruvate was started when the flask inside temperature exceeded 70° C., and that after completion of said addition, the reaction was further continued for 4 hours at a temperature of 80° C. under reflux of benzene. At 6 hours after start of the reaction, the conversion of methyl phenylpyruvate was 32 percent and the selectivity toward methyl α-(hexanoylamino)cinnamate was 85 mole percent based on the converted methyl phenylpyruvate.

What we claim is:

1. A method of producing L-phenylalanine which comprises bringing, in the presence of water, an N-acylphenylalanine alkyl ester in L form into contact with an aminoacylase capable of hydrolyzing said N-acylphenylalanine alkyl ester in L form into L-phenylalanine, to thereby cause formation of L-phenylalanine, said N-acylphenylalanine alkyl ester having the formula $$\text{C}_6\text{H}_5\text{—CH}_2\text{CH(NHCOCH}_2\text{R}^2\text{)—COOR}^1$$

wherein $R^1$ is a lower alkyl group and $R^2$ is a hydrogen atom, a lower alkyl group or a halogen atom.

2. The method of claim 1, wherein said N-acylphenylalanine alkyl ester in L form is brought into contact with said aminoacylase in the form of a mixture of said N-acylphenylalanine alkyl ester in L form and the corresponding N-acylphenylalanine alkyl ester in D form.

3. The method of claim 2, wherein said mixture is the racemic modification of the N-acylphenylalanine alkyl ester.

4. The method of claim 2, wherein said mixture of the L and D forms of the N-acylphenylalanine alkyl ester is the product of racemization obtainable by treating the N-acylphenylalanine alkyl ester obtained by the enzymatic reaction according to claim 1 and having an L form proportion of less than 50 percent, with a strongly basic amine.

5. The method of claim 4, wherein said strongly basic amine is an amine showing a pH of not less than 12.0 at 25° C. in an aqueous solution thereof in a concentration of 0.1 mole per liter.

6. The method of claim 5, wherein said strongly basic amine is an amine showing a pH of not less than 12.5 at 25° C. in an aqueous solution thereof in a concentration of 0.1 mole per liter.

7. The method of claim 6, wherein said strongly basic amine is 1,8-diazabicyclo[5.4.0]undecene-7, 1,5-diazabicyclo[4.3.0]nonene-5 or 1,1,3,3-tetramethylguanidine.

8. The method of claim 2, wherein said N-acylphenylalanine alkyl ester in the form of a mixture of L form and D form is prepared by a process comprising the steps of (i) reacting benzaldehyde with an α-haloacetic acid ester of the general formula $$\text{X—CH}_2\text{COOR}^1$$

wherein X is a chlorine or bromine atom and $R^1$ is as defined above, in the presence of potassium carbonate or potassium hydrogen carbonate and of a polyoxyalkylene compound containing, on the average, at least three oxyethylene units per molecule, while removing the resulting water from the reaction system, (ii) isomerizing the resulting phenylglycidic acid ester of the general formula $$\text{C}_6\text{H}_5\text{—CH(—O—)CH—COOR}^1$$

wherein $R^1$ is as defined above, to a phenylpyruvic acid ester of the general formula $$\text{C}_6\text{H}_5\text{—CH}_2\text{C(=O)COOR}^1$$

wherein $R^1$ is as defined above, (iii) reacting said phenylpyruvic acid ester with an acid amide of the general formula $$\text{R}^2\text{CH}_2\text{CONH}_2$$

wherein $R^2$ is as defined above, in an amount of not more than 3 moles per mole of said phenylpyruvic acid ester in the presence of an acid having a pKa value of not more than 3 at a temperature of 100°-200° C. while removing the resulting water from the reaction system, to give an α-(acylamino)cinnamic acid ester of the general formula

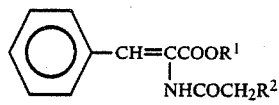

wherein R¹ and R² are as defined above, and (iv) hydrogenating said α-(acylamino)cinnamic acid ester.

9. The method of claim 8, wherein said polyoxyalkylene compound is an acyclic polyoxyalkylene compound.

10. The method of claim 9, wherein said acyclic polyoxyalkylene compound is represented by the general formula

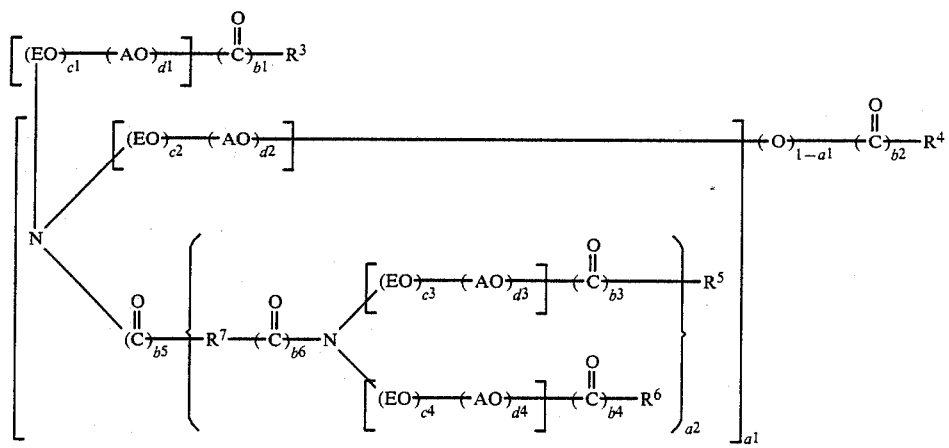

wherein $R^3$, $R^4$, $R^5$ and $R^6$ are each independently a hydrogen atom or an alkyl, cycloalkyl, aryl or aralkyl group containing 1-15 carbon atoms, which may optionally be substituted, $R^7$ is a straight-chain or branched-chain alkylene group containing 1-12 carbon atomes, E is an ethylene group, A is a propylene group [—CH(CH₃)CH₂—], $a^1$ and $a^2$ are each independently an integer of 0 or 1, $b^1$, $b^2$, $b^3$, $b^4$, $b^5$ and $b^6$ are each independently an integer of 0 or 1, $c^1$, $c^2$, $c^3$, $c^4$, $d^1$, $d^2$, $d^3$ and $d^4$ are each independently a number not less than 0 provided that the average value of $(c^1+c^2+c^3+c^4)$ is within the range of 3-100, that the average value of $(d^1+d^2+d^3+d^4)$ is within the range of 0-100 and that the average value of $(c^1+c^2+c^3+c^4)$ is not less than the average value of $(d^1+d^2+d^3+d^4)$, and, in the $\{(OE)_{\overline{cm}}(OA)_{\overline{dm}}\}$ groups (m being 1, 2, 3 or 4), the $c^m$ —OE— units and $d^m$ —OA—units may be arranged in any order.

11. The method of claim 10, wherein the acyclic polyoxyalkylene compound is selected from the group consisting of polyethylene glycol containing, on the average, 5-50 oxyethylene units per molecule, dialkyl ethers thereof, polyoxyethylenepolyoxypropylene glycol of the general formula

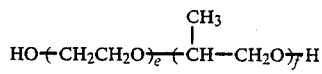

wherein e is a number on the average, within the range of 8-40 and is not less than f and (e+f) is a number, on the average, within the range of 10-70 and wherein the e oxyethylene units and f oxypropylene units may be arranged in any order, and dialkyl ethers thereof.

12. The method of claim 11, wherein the acyclic polyoxyalkylene compound is polyethylene glycol containing, on the average, 10-50 oxyethylene units per molecule, or the dimethyl ether thereof.

13. The method of claim 8, wherein the water formed in the reaction of benzaldehyde and α-haloacetic acid ester in step (i) is removed from the reaction system in the form of an azeotrope.

14. The method of claim 8, wherein potassium carbonate or potassium hydrogen carbonate is used in an amount of about 1-2.3 gram equivalents per mole of benzaldehyde.

15. The method of claim 14, wherein potassium carbonate or potassium hydrogen carbonate is used in an amount of about 1.1-2.0 gram equivalents per mole of benzaldehyde.

16. The method of claim 8, wherein, in step (ii), the isomerization of phenylglycidic acid ester is carried out in the presence of an acid.

17. The method of claim 16, wherein, in carrying out the isomerization in step (ii), a sulfonic acid or a sulfonic acid type cation exchange resin is used as the acid.

18. The method of claim 8, wherein, in step (iii), the acid amide is used in an amount of about 1.2-2.5 moles per mole of the phenylpyruvic acid ester.

19. The method of claim 8, wherein, in carrying out the reaction in step (iii), sulfuric acid, a sulfonic acid or a sulfonic acid type cation exchange resin is used as the acid.

20. The method of claim 8, wherein the reaction in step (iii) is carried out at a temperature within the range of 120°-160° C.

21. The method of claim 8, wherein the reaction in step (iii) is carried out while maintaining the concentration of phenylpyruvic acid ester at a level not higher than about 1.0 mole per liter of the reaction mixture.

22. The method of claim 8, wherein the water formed in the reaction in step(iii) is removed from the reaction system in the form of an azeotrope.

23. The method of claim 8, wherein, in step (iv), the hydrogenation of α-(acylamino)cinnamic acid ester is carried out in the presence of a palladium catalyst or a nickel catalyst.

24. The method of claim 8, wherein the hydrogenation in step (iv) is carried out in the presence of a tertiary amine.

25. The method of claim 1, wherein said aminoacylase is derived from a fungus belonging to the genus Aspergillus.

26. The method of claim 1, wherein the reaction mixture obtainable by bringing the L-form of N-acylphenylalanine alkyl ester into contact with the aminoacylase is then brought into contact with an organic solvent substantially immiscible with water to thereby extract the remaining L-form of N-acylphenylalanine alkyl ester or the D-form of N-acylphenylalanine alkyl ester or a mixture of these into the organic layer.

27. The method of claim 1, wherein the L-form of N-acylphenylalanine alkyl ester is brought into contact with the aminoacylase in the presence of water and an organic solvent substantially immiscible with water.

28. The method of claim 26 or 27, wherein said organic solvent comprises at least one organic solvent selected from the group consisting of halogenated hydrocarbons, nitriles containing not less than 3 carbon atoms, carboxylic acid esters containing not less than 4 carbon atoms, ketones containing not less than 5 carbon atoms, ethers containing not less than 5 carbon atoms, aromatic hydrocarbons containing not less than 6 carbon atoms, alcohols containing not less than 6 carbon atoms, phosphoric acid triesters containing not less than 8 carbon atoms and tertiary amines containing not less than 8 carbon atoms in which at least one of the substituents on nitrogen atom is an aromatic hydrocarbon residue 29. The method of claim 27, wherein L-phenylalanine crystals are separated from the reaction mixture obtainable by bringing the L-form of N-acylphenylalanine alkyl ester into contact with the aminoacylase and the aqueous layer containing the aminoacylase recycled to the step of bringing the L-form of N-acylphenylalanine alkyl ester into contact with the aminoacylase.

* * * * *